(12) United States Patent
Park et al.

(10) Patent No.: US 8,907,047 B2
(45) Date of Patent: Dec. 9, 2014

(54) WATER-SOLUBLE POLYMER AND WATER-SOLUBLE NANOPARTICLE COMPOSITE

(75) Inventors: Joonsik Park, Kamakura (JP); Masashi Higasa, Kamakura (JP); Asako Sogame, Kamakura (JP)

(73) Assignee: Toray Industries, Inc. (JP)

( * ) Notice: Subject to any disclaimer, the term of this patent is extended or adjusted under 35 U.S.C. 154(b) by 207 days.

(21) Appl. No.: 13/703,237

(22) PCT Filed: Jun. 24, 2011

(86) PCT No.: PCT/JP2011/064503
§ 371 (c)(1),
(2), (4) Date: Dec. 10, 2012

(87) PCT Pub. No.: WO2011/162366
PCT Pub. Date: Dec. 29, 2011

(65) Prior Publication Data
US 2013/0075665 A1 Mar. 28, 2013

(30) Foreign Application Priority Data

Jun. 25, 2010 (JP) .................................. 2010-145340

(51) Int. Cl.
| | |
|---|---|
| H01B 1/20 | (2006.01) |
| C09D 5/23 | (2006.01) |
| C08G 73/06 | (2006.01) |
| C08G 73/02 | (2006.01) |
| B82Y 5/00 | (2011.01) |
| B82Y 40/00 | (2011.01) |
| C08L 79/02 | (2006.01) |
| B82Y 30/00 | (2011.01) |

(52) U.S. Cl.
CPC ................ *C08G 73/0233* (2013.01); *B82Y 5/00* (2013.01); *B82Y 40/00* (2013.01); *C08L 79/02* (2013.01); *B82Y 30/00* (2013.01); *Y10S 977/773* (2013.01)

USPC ..... 528/363; 528/403; 528/423; 252/62.51 R; 252/301.36; 252/518.1; 252/582; 977/773

(58) Field of Classification Search
CPC .............. H01B 1/02; H01B 1/08; H01B 1/10; H01B 1/20; H01B 1/22; C09D 5/23; C09K 11/02; C08G 65/00; C08G 73/00; C08G 73/04; C08G 73/06
USPC ................... 528/363, 403, 423; 252/62.51 R, 252/301.36, 518.1, 582
See application file for complete search history.

(56) References Cited

U.S. PATENT DOCUMENTS

| | | | |
|---|---|---|---|
| 8,366,916 B2* | 2/2013 | Lee .............................. | 208/263 |
| 8,445,017 B2* | 5/2013 | Slobodkin et al. ............ | 424/486 |

(Continued)

FOREIGN PATENT DOCUMENTS

| | | |
|---|---|---|
| JP | 02-172920 | 7/1990 |
| JP | 2005-226032 A | 8/2005 |

(Continued)

OTHER PUBLICATIONS

Yu, William W., et al., "Forming Biocompatible and Nonaggregated Nanocrystals in Water Using Amphiphilic Polymers," *J. Am. Chem. Soc.*, 2007, 129, pp. 2871-2879.

(Continued)

*Primary Examiner* — Mark Kopec
(74) *Attorney, Agent, or Firm* — DLA Piper LLP (US)

(57) ABSTRACT

A water-soluble nanoparticle complex has a plurality of accumulated nanoparticles and has excellent uniformity and stability by forming a complex of nanoparticles using a water-soluble polymer and which allows for use of nanoparticles in biochemical applications.

20 Claims, 7 Drawing Sheets

(56) References Cited

U.S. PATENT DOCUMENTS

| | | |
|---|---|---|
| 2009/0098663 A1 | 4/2009 | Han et al. |
| 2009/0156782 A1 | 6/2009 | Kataoka et al. |
| 2009/0198009 A1 | 8/2009 | Matsuki et al. |

FOREIGN PATENT DOCUMENTS

| | | |
|---|---|---|
| JP | 2005-298542 A | 10/2005 |
| JP | 2006-213592 | 8/2006 |
| JP | 2008-540726 | 11/2008 |
| JP | 2011-102332 A | 5/2011 |
| WO | 00/17642 | 3/2000 |
| WO | 2007/026932 A1 | 9/2007 |
| WO | 2008/018123 A1 | 2/2008 |

OTHER PUBLICATIONS

Dubertret, Benoit, et al., "In Vivo Imaging of Quantum Dots Encapsulated in Phospholipid Micelles," *Science*, Nov. 29, 2002, vol. 298, pp. 1759-1761.

Anderson, Robin E., et al., "Systematic Investigation of Preparing Biocompatible, Single, and Small ZnS-Capped CdSe Quantum Dots with Amphiphilic Polymers," *ACS Nano*, 2008 2 (7), pp. 1341-1352.

Smith, Andrew M., et al., "Minimizing the Hydrodynamic Size of Quantum Dots with Multifunctional Multidentate Polymer Ligands," *J. Am. Chem. Soc.*, 2008 130 (134), pp. 11278-11279.

Gao, Xiaohu, et al., "Doping Mesoporous Materials with Multicolor Quantum Dots," *J. Phys. Chem. B*, 2003, 107, pp. 11575-11578.

\* cited by examiner (a) BF-STEM    (b) HAADF-STEM (a) AFM Height Image    (b) AFM Phase Image

WATER-SOLUBLE POLYMER AND WATER-SOLUBLE NANOPARTICLE COMPOSITE

RELATED APPLICATIONS

This is a §371 of International Application No. PCT/JP2011/064503, with an international filing date of Jun. 24, 2011 (WO 2011/162366 A1, published Dec. 29, 2011, which is based on Japanese Patent Application No. 2010-145340 filed Jun. 25, 2010, the subject matter of which is incorporated herein by reference.

TECHNICAL FIELD

This disclosure relates to a novel water-soluble polymer and a water-soluble nanoparticle complex comprising the water-soluble polymer and nanoparticles.

BACKGROUND

In recent years, synthesis and property evaluation of nanoparticles having any properties of magnetic properties, luminescence properties, and plasmon absorption properties have been intensively studied. Nanoparticles that exhibit various sizes, compositions, polarities and solubilities, surface conditions, and the like have been developed, and, in particular, in terms of biochemical application, semiconductor nanoparticles and metal nanoparticles have received attention due to their distinctive optical properties. In particular, organic fluorescent dyes and the like have been commonly used as a detection label in existing biotools, but they have problems, for example, with luminescence properties, stability, and cost. Thus, recently, studies on the use of semiconductor nanoparticles having high luminescence and high stability as a detection label have received attention (see WO 00/017642).

To use nanoparticles in biochemical applications, it is necessary that the nanoparticles have excellent surface hydrophilicity and biocompatibility and that the nanoparticle properties be retained even in an aqueous solution. For the conventional method for water-solubilizing nanoparticles using a low molecular-weight solubilizer (see Dubertret, B. et al., SCIENCE, 2002, 298, 1759-1762), various problems have been pointed out: for example, hydrophilic functional groups introduced onto a nanoparticle surface are removed, or functional groups having an electric charge affect the nanoparticle surface to decrease the water dispersion stability, light stability, and the like of nanoparticles (see Yu, W. W. et al., J. AM. CHEM. SOC., 2007, 129, 2871-2879). There is also a method in which nanoparticles are encapsulated in microspheres, liposomes, hydrogels, or the like, but the development of its application is limited because of the too large size (see GaO, X. et al., J. Phys. Chem. B., 2003, 107, 11575-11578).

As a means for solving the above-mentioned problems, the method of coating a nanoparticle with polymers is known (see JP 2006-213592 A, JP 2008-540726 W, Anderson, R. E. et al., ACS NANO, 2008, 2, 1341-1352 and Andrew, M. S. et al., J. AM. CHEM. SOC., 2008, 130, 11278-11279). For example, by using an amphiphilic polymer having a side chain comprising a hydrophilic carboxyl group and a hydrophobic lipid-soluble compound, stable binding through interaction with a hydrophobic surface of nanoparticles is achieved, and the hydrophilic group can be used for water-solubilization of the nanoparticles and as a site for introducing biomolecules (see Anderson, R. E. et al., ACS NANO, 2008, 2, 1341-1352). On the other hand, the case has also been reported where, a single nanoparticle is coated compactly with a plurality of polymers to improve the water dispersion stability, light stability, and the like using, in place of the hydrophobic lipid-soluble compound, ligand exchange reaction between a nanoparticle surface and vinyl-based water-soluble polymers into the side chain of which a thiol group and an amino group are introduced (see Andrew, M. S. et al., J. AM. CHEM. SOC., 2008, 130, 11278-11279). However, in any of these cases, a plurality of polymers are associated with one nanoparticle, and thus it has been difficult to improve total emission intensity and the like of nanoparticles by accumulating a number of nanoparticles on one surface ligand by uniform complexation of a plurality of nanoparticles and polymers.

It could therefore be helpful to provide a water-soluble nanoparticle complex that allows for the use of nanoparticles for biochemical purposes.

SUMMARY

We discovered that a water-soluble nanoparticle complex in which a plurality of nanoparticles are accumulated and which has a uniform particle size can be formed by using a water-soluble polymer in which a hydrophilic functional group and a functional group that can be bound by ligand exchange reaction with a nanoparticle surface are added to a linear polyethyleneimine.

We thus provide [1] to [11] below:

[1] A water-soluble polymer, comprising:
a repeating unit represented by Formula (1) below:

(wherein $R_1$ is —COOH, —OH, or —(OCH$_2$CH$_2$)$_p$R' (wherein R' is —COOH, —OH, —CH=CH$_2$, —C≡CH, or —N$_3$, and p is an integer from 1 to 30.), and l is an integer from 1 to 10.),
a repeating unit represented by Formula (2) below:

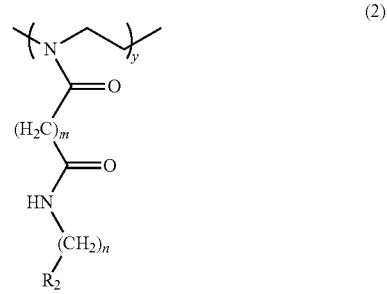

(wherein $R_2$ is —SR$_3$ or —NHR$_4$ (wherein $R_3$ is hydrogen or a thiol-protecting group selected from the group consisting of benzyl, methoxybenzyl, N-(acetyl)aminomethyl, t-butyl, methylbenzyl, 3,4-dimethylbenzyl, triphenylmethyl, benzhydryl, acetamidomethyl, carbomethoxysulfenyl, 3-nitro-2-pyridinesulfenyl, ethylcarbamoyl, 9-fluorenylmethyl, and pyridyl sulfide, and $R_4$ is hydrogen or an amino-protecting group selected from tert-butoxycarbonyl, benzyloxycarbonyl, 9-fluorenylmethyloxycarbonyl, 2,2,2-trichloroethoxycarbonyl, allyloxycarbonyl, phthaloyl, p-toluenesulfonyl, and 2-nitrobenzenesulfonyl.); a, the number of repeating units containing —SR$_3$, and b, the number of repeating units containing —NHR$_4$, in y, the number of repeating units, satisfy b/a+b=0 to 0.60; and m and n are an integer from 1 to 10.), and a repeating unit represented by Formula (3) below:

wherein x, the number of repeating units of Formula (1), y, the number of repeating units of Formula (2), and z, the number of repeating units of Formula (3) above, satisfy x/(x+y+z)= 0.01 to 0.70, y/(x+y+z)=0.20 to 0.70, and z/(x+y+z)=0.01 to 0.70.

[2] The water-soluble polymer according to [1], wherein x, y, and z satisfy x+y+z=10 to 350.

[3] The water-soluble polymer according to [1] or [2], wherein at least one end of a polymer main chain composed of the repeating units of Formulas (1), (2), and (3) comprises at least one functional group selected from the group consisting of —NH$_2$, —COOH, —OH, —SH, —CHO, and biotinyl.

[4] The water-soluble polymer according to [3], comprising —(OCH$_2$CH$_2$)$_p$— (wherein p is an integer from 1 to 120) as a spacer between the polymer main chain and the above-described functional group.

[5] A water-soluble nanoparticle complex, comprising the water-soluble polymer according to any one of [1] to [4] and nanoparticles.

[6] The water-soluble nanoparticle complex according to [5], wherein the water-soluble nanoparticle complex has an average particle size of 10 to 300 nm.

[7] The water-soluble nanoparticle complex according to [5] or [6], wherein the nanoparticles have luminescence properties, plasmon absorption properties, or magnetic properties.

[8] The water-soluble nanoparticle complex according to any one of [5] to [7], wherein the nanoparticles are gold nanoparticles or semiconductor nanoparticles.

[9] The water-soluble nanoparticle complex according to [8], wherein the semiconductor nanoparticles are semiconductor nanoparticles comprising at least a Group 12 element of the periodic table and a Group 16 element of the periodic table, semiconductor nanoparticles comprising a Group 11 element of the periodic table, a Group 13 element of the periodic table, and a Group 16 element of the periodic table, or semiconductor nanoparticles comprising a Group 13 element of the periodic table and a Group 15 element of the periodic table.

[10] A method of producing a water-soluble nanoparticle complex, wherein nanoparticles and the water-soluble polymer according to any one of [1] to [4] are mixed in an organic solvent.

[11] A reagent containing the water-soluble nanoparticle complex according to any one of [5] to [8].

The water-soluble polymer allows for the formation of a water-soluble nanoparticle complex in which a plurality of nanoparticles are accumulated and which has a generally uniform particle size. In addition, the water-soluble nanoparticle complex can be used in biochemical applications because it has water dispersion stability and is characterized by maintaining the properties of nanoparticles such as fluorescence stability over a long period of time.

DETAILED DESCRIPTION

Synthesis of Water-Soluble Polymer

Figure 1:
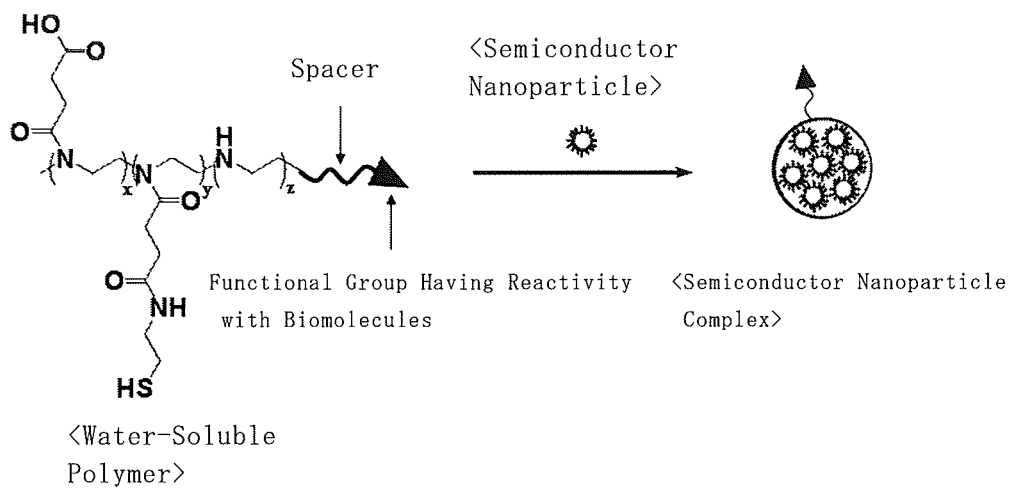
FIG. 1 is a scheme for forming a water-soluble nanoparticle complex.

The water-soluble polymer is characterized by having a segment that has a hydrophilic functional group, the segment being composed of the repeating unit represented by Formula (1) above, a segment that comprises a functional group that can be bound by ligand exchange reaction with nanoparticles (hereinafter referred to as a ligand exchange reactive group), the segment being composed of the repeating unit represented by Formula (2) above, and a segment composed of the repeating unit represented by Formula (3) above.

The segment that has a hydrophilic functional group, the segment being composed of the repeating unit represented by Formula (1) above, has a hydrophilic functional group ($R_1$)

having a biomolecule-binding capacity. Specific examples of $R_1$ include —COOH, —OH, and $(OCH_2CH_2)_pR'$ (wherein R' is —COOH, —OH, —CH=CH$_2$, —C≡CH, or N$_3$, and p is an integer from 1 to 30.); —COOH, —OH, or $(OCH_2CH_2)_pR'$ (wherein R' is —COOH or —OH, and p is an integer from 1 to 5.) is preferred; and —COOH is more preferred. l is an integer from 1 to 10, and, preferably, l is an integer from 2 to 4.

The segment that comprises a ligand exchange reactive group ($R_2$), the segment being composed of the repeating unit represented by Formula (2) above, has a moiety comprising —SH or —NH$_2$ which can undergo ligand exchange reaction with a hydrophilic low-molecular surface of a nanoparticle. In the segment that comprises a ligand exchange reactive group ($R_2$), the segment being composed of the repeating unit represented by Formula (2) above, a, the number of repeating units containing —SH, and b, the number of repeating units containing —NH$_2$, satisfy b/a+b=0 to 0.60 and preferably 0 to 0.51. m and n are an integer from 1 to 10, and, preferably, m and n are an integer from 2 to 4.

The segment composed of the repeating unit represented by the chemical formula (3) above is a segment composed of polyethyleneimine. Namely, the water-soluble polymer has a structure in which a polyethyleneimine backbone is provided with a substituent constituting the segment comprising a hydrophilic functional group and a substituent constituting the segment comprising a ligand exchange reactive group.

The composition ratio of each segment described above, when taking the number of the repeating unit represented by Formula (1) above as x, the number of the repeating unit represented by Formula (2) above as y, and the number of the repeating unit represented by Formula (3) above as z (x, y, and z are an integer), is characterized by satisfying x/(x+y+z)= 0.01 to 0.70, y/(x+y+z)=0.20 to 0.70, and z/(x+y+z)=0.01 to 0.70, preferably x/(x+y+z)=0.04 to 0.70, y/(x+y+z)=0.20 to 0.65, and z/(x+y+z)=0.01 to 0.65, more preferably x/(x+y+z)= 0.20 to 0.70, y/(x+y+z)=0.20 to 0.60, and z/(x+y+z)=0.01 to 0.20, and still more preferably x/(x+y+z)=0.27 to 0.66, y/(x+y+z)=0.22 to 0.59, and z/(x+y+z)=0.01 to 0.18. When x, y, and z are beyond these numerical ranges, complexation efficiency of the water-soluble nanoparticle complex will decrease, which is not preferred. x/(x+y+z), y/(x+y+z), and z/(x+y+z) can be calculated based on the $^1$H-NMR spectrum of a water-soluble polymer (see Examples).

The sum of x, y, and z which represents the size of the water-soluble polymer, i.e., the degree of polymerization (DP) of the water-soluble polymer is not particularly restricted and is preferably in the range of 10 to 350 and more preferably in the range of 20 to 320 in view of the fact that the average particle size of the water-soluble nanoparticle complex mentioned below is controlled by the sum of x, y, and z and that the average particle size of the water-soluble nanoparticle complex is preferably not more than 300 nm. The degree of polymerization (DP) of the water-soluble polymer can be measured by $^1$H-NMR spectrum (see Examples).

The water-soluble polymer can be obtained by the step of introducing the segment of a hydrophilic functional group ($R_1$) by reacting a linear polyethyleneimine having a polydispersity index (PDI: weight average molecular weight (Mw)/ number average molecular weight (Mn)) of 1.3 or less with a fatty acid anhydride or a fatty acid halide comprising a hydrophilic reactive group and the step of introducing a ligand exchange reactive group ($R_2$) by reacting the linear polyethyleneimine with a fatty acid halide comprising a ligand exchange reactive group. The polydispersity index (PDI) of the linear polyethyleneimine can be measured by gel permeation chromatography (GPC) diagram.

In the step of introducing a hydrophilic functional group described above, the fatty acid anhydride comprising a hydrophilic functional group, when used, is not particularly limited as long as a desired structure can be introduced into a linear polyethyleneimine, and examples thereof include a linear fatty acid anhydride represented by Formula (4) below:

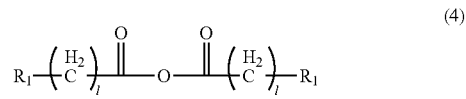

(4)

(wherein $R_1$ and l are as defined above.).

A portion of $R_1$ may be protected during the reaction; for example, —COOH can be protected by any of methyl/ethyl ester, benzyl ester, tert-butyl ester, and tert-butyldimethylsilyl, and —OH can be protected by any of methyl, benzyl, p-methoxybenzyl, tert-butyl, methoxymethyl (MOM), 2-tetrahydropyranyl (THP), ethoxyethyl (EE), acetyl, pivaloyl, benzoyl, trimethylsilyl (TMS), triethylsilyl (TES), tert-butyldimethylsilyl (TBS or TBDMS), triisopropylsilyl (TIPS), and tert-butyldiphenylsilyl (TBDPS).

When —COOH is introduced as $R_1$, a cyclic anhydride of dicarboxylic acid represented by Formula (5) below, preferably, succinic acid anhydride, glutaric acid anhydride, or adipic acid anhydride can be used:

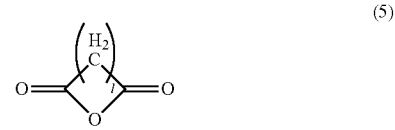

(5)

(wherein l is as defined above.).

In the step of introducing a hydrophilic functional group described above, the fatty acid halide comprising a hydrophilic reactive group, when used, is not particularly limited as long as a desired structure can be introduced into a linear polyethyleneimine, the suitable examples thereof include a compound represented by Formula (6) below:

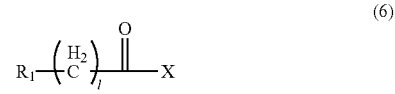

(6)

(X = Cl, Br)

(wherein $R_1$ and l are as defined above.).

A portion of $R_1$ may be protected during the reaction as described above.

In the step of introducing a ligand exchange reactive group described above, the fatty acid halide comprising a ligand exchange reactive group, when used, is not particularly limited as long as a desired structure can be introduced into a linear polyethyleneimine, and a compound represented by Formula (7) below can be preferably used:

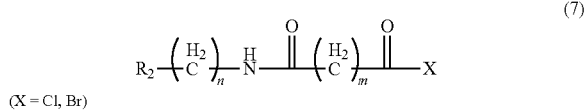

(X = Cl, Br)

(wherein $R_2$, m, and n are as defined above.).

$R_2$ may be protected during the reaction; for example, —SH may be protected by any of benzyl, methoxybenzyl, N-(acetyl)aminomethyl, t-butyl, methylbenzyl, 3,4-dimethylbenzyl, triphenylmethyl, benzhydryl, acetamidomethyl, carbomethoxysulfenyl, 3-nitro-2-pyridinesulfenyl, ethylcarbamoyl, 9-fluorenylmethyl, or pyridyl sulfide, and —NH$_2$ may be protected by any of tert-butoxycarbonyl, benzyloxycarbonyl, 9-fluorenylmethyloxycarbonyl, 2,2,2-trichloroethoxycarbonyl, allyloxycarbonyl, phthaloyl, p-toluenesulfonyl, or 2-nitrobenzenesulfonyl.

In particular, when —COOH is introduced as the hydrophilic reactive group $R_1$ described above, a ligand exchange reactive group can be introduced by the step of reacting the —COOH with an amine compound comprising the ligand exchange reactive group described above. Specifically, a portion of the hydrophilic reactive group introduced can be converted to a ligand exchange reactive group by condensing —COOH with an amine compound represented by Formula (8) below, preferably, 2-mercaptoethylamine, 3-mercaptopropylamine, 4-mercaptobutylamine, ethylenediamine, propylenediamine, or butylenediamine:

(wherein $R_2$ and n are as defined above.).

A portion of $R_2$ may be protected during the reaction as described above.

The composition ratio of each segment in the water-soluble polymer, i.e., x (the number of repeating units represented by Formula (1) above):y (the number of repeating units represented by Formula (2) above):z (the number of repeating units represented by Formula (3) above) can be controlled by reacting a secondary amine of a linear polyethyleneimine sequentially with a fatty acid anhydride or a fatty acid halide comprising a hydrophilic reactive group and with a fatty acid halide or an amine compound comprising a ligand exchange reactive group to a desired ratio. Specific examples include the method of controlling the composition ratio of x:y:z by reacting a secondary amine of a linear polyethyleneimine with a linear fatty acid anhydride comprising a hydrophilic functional group represented by the chemical formula (4) above to introduce x and then with a fatty acid halide comprising a ligand exchange reactive group represented by the chemical formula (7) above to introduce y, the method of controlling the composition ratio of x:y:z by reacting a secondary amine of a linear polyethyleneimine with a fatty acid halide comprising a hydrophilic functional group represented by the chemical formula (6) above to introduce x and then with a fatty acid halide comprising a ligand exchange reactive group represented by the chemical formula (7) above to introduce y, and the method of controlling the composition ratio of x:y:z by reacting a secondary amine of a linear polyethyleneimine with a cyclic anhydride of dicarboxylic acid represented by the chemical formula (5) above to introduce x and then reacting the carboxyl group with an amine compound comprising a ligand exchange reactive group represented by the chemical formula (8) above to introduce y, and the like.

In the water-soluble polymer, at least one end of a polymer main chain composed of the repeating units of Formulas (1), (2), and (3) above preferably comprises at least one functional group selected from the group consisting of —NH$_2$, —COOH, —OH, —SH, —CHO, and biotinyl, which are functional groups having a biomolecule-binding capacity. Examples of the biomolecules here include nucleic acids such as DNA and RNA, proteins, peptides, saccharides, lipids, and hormones; nucleic acids or proteins are preferred, and nucleic acids are more preferred.

When the biomolecule is a nucleic acid, introduction of a reactive group into a portion of the nucleic acid and reaction of the reactive group with a surface functional group of a complex allows for binding to the nucleic acid. For example, a double-stranded nucleic acid having a terminal amino group can be produced by carrying out a polymerase chain reaction (PCR) using as a primer an oligonucleotide having a terminal amino group. Condensation reaction of the terminal amino group of the nucleic acid with the carboxyl group introduced onto the complex surface allows for binding of the complex to the nucleic acid. When the biomolecule is a protein, binding an amino group of a lysine residue in the protein to a carboxyl group on a complex surface allows for binding of the complex to the protein. Further, when using a complex having a biotinyl group, avidin-biotin interaction allows for immobilization on avidin molecules. Since avidin has four binding sites in one molecule, for example, avidin is first bound to a nucleic acid into which a biotinyl group is introduced, and further a complex having a biotinyl group on its surface is allowed to act on the end binding site of the avidin, thereby allowing for labeling of the nucleic acid with the complex. On the other hand, when using a complex having a primary amino group, avidin molecules can be directly immobilized as a complex surface ligand not through a biotinyl group, and thus reduction in binding strength in the dyeing method using biotin-avidin sandwich structure can be inhibited.

Further, the water-soluble polymer preferably comprises —(OCH$_2$CH$_2$)$_p$— (p is an integer from 1 to 120) as a spacer between the polymer main chain composed of the repeating units of Formulas (1), (2), and (3) above and the functional group described above. This spacer is assumed to have as a hydrophilic group the function of improving water dispersion stability of a complex and biomolecule-binding capacity of the above-described functional group introduced onto a surface.

Introduction of the above-mentioned functional group or spacer having a functional group into at least one end of the polymer main chain composed of the repeating units of Formulas (1), (2), and (3) above is achieved by the step of polymerizing a linear polyoxazoline represented by Formula (9) below using an oxazoline derivative, a cation polymerization initiator, and a nucleophilic terminator, the step of introducing the above-mentioned functional group or spacer having a functional group into at least one end of the linear polyoxazoline main chain, and the step of conversion into a linear polyethyleneimine by side-chain deprotection and side-chain conversion reaction using compounds of Formulas (4) to (7) above:

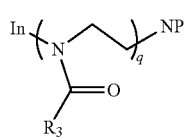 (9)

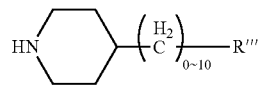 (10)

(wherein In represents a residue deriving from a cation polymerization initiator; NP represents a residue deriving from a nucleophilic terminator; $R_3$ is linear or branched $C_1$-$C_{20}$ alkyl (preferably, methyl, ethyl, propyl, isopropyl, butyl, t-butyl, sec-butyl, hexyl, octyl, dodecyl, octadecyl, eicosyl, and 18-methylnonadecanyl); and q is the sum of x, y, and z above (preferably an integer from 10 to 350).).

In, a residue deriving from a cation polymerization initiator, is not particularly limited as long as it is a residue of a cation polymerization initiator that is capable of introducing the above-mentioned functional group or spacer having a functional group into the initial end of a polymer main chain composed of the repeating units of Formulas (1), (2), and (3) above. Similarly, NP, a residue deriving from a nucleophilic terminator, is not particularly limited as long as it is a residue of a nucleophilic terminator that is capable of providing a functional group and a spacer to the terminal end of a polymer main chain composed of the repeating units of Formulas (1), (2), and (3) above.

By using a cation polymerization initiator having a functional group or a spacer to which a functional group has been added in advance, the step of polymerizing the linear polyoxazoline represented by Formula (9) above and the step of introducing the above-mentioned functional group or spacer having a functional group into at least one end of the linear polyoxazoline main chain may be carried out at one time. Similarly, by using a nucleophilic terminator having a functional group or a spacer to which a functional group has been added in advance, the step of polymerizing the linear polyoxazoline represented by Formula (9) above and the step of introducing a functional group or a spacer to which a functional group is added into at least one end of the linear polyoxazoline main chain may be carried out at one time.

Examples of the cation polymerization initiator described above include various tosylates represented by Formula: TsOR, and specific examples of the residue corresponding to an R group include, but are not limited to, for example, —$(CH_2)_{1-10}R'$ (wherein R' is —$NH_2$, —COOH, —OH, —SH, —CHO, or biotinyl.) and —$(OCH_2CH_2)_pR'$ (wherein R' is —$NH_2$, —COOH, —OH, —SH, —CHO, or biotinyl, and p is an integer from 1 to 120.). A portion of R' may be protected during the polymerization reaction so as not to adversely affect the cation ring-opening polymerization of oxazoline; for example, —$NH_2$, —COOH, —OH, and —SH can be protected as described above, and —CHO can be protected by any of dimethyl acetal, cyclic acetal, and dithioacetal.

Examples of the nucleophilic terminator described above include anionoid compounds which generate an anionically active end corresponding to the NP residue described above, and specific examples thereof include, but are not limited to, for example, $H_2O$, NaOH, KOH, NaSH, KSH, $NH_3$, NHR'R" (wherein R' is hydrogen or $C_1$-$C_{10}$ alkyl, and R" is —$(CH_2)_{1-10}R'''$ (wherein R''' is —$NH_2$, —COOH, —OH, —SH, —CHO, or biotinyl group.) or —$(OCH_2CH_2)_pR'''$ (wherein R''' is as defined above, and p is an integer from 1 to 120.), and derivatives of a cyclic secondary amine compound represented by Formula (10) below. A portion of R''' may be protected during the reaction as described above:

(wherein R''' is as defined above.).

[Preparation of Water-Soluble Nanoparticle Complex]

Nanoparticles are fine particles of a substance having a nanometer-scale size, and it is known that there exist nanoparticles exhibiting properties that are particularly useful in various industrial applications, specifically, magnetic properties, luminescence properties, or plasmon absorption properties). The water-soluble polymer described above can be used to form nanoparticles into a water-soluble nanoparticle complex.

The water-soluble nanoparticle complex (hereinafter also referred to simply as "the complex") refers to a complex formed by stable association of the above-mentioned nanoparticles and water-soluble polymer, and the complex has the effect of improving the properties of the nanoparticles because a plurality of nanoparticles are accumulated in one water-soluble nanoparticle complex. Specifically, when luminescent nanoparticles are formed into a water-soluble nanoparticle complex, the water-soluble nanoparticle complex has the effect of improving emission intensity per particle (see FIG. 1). In comparison with vinyl-based water-soluble polymers known as a water-soluble polymer for water-solubilization of nanoparticles, the water-soluble polymer of the present invention having a polyethyleneimine-based backbone is assumed to be effective for formation of a complex that accumulates a plurality of nanoparticles because the backbones tends to form a crystal structure.

The average particle size of nanoparticles to be formed into a water-soluble nanoparticle complex is, in view of the expression of the quantum size effect of the nanoparticles, preferably 1 to 100 nm, more preferably 1 to 50 nm, and, in view of reaction with biomolecules, still more preferably 1 to 10 nm. The size of the nanoparticles can be measured by observation under an electron microscope. Specifically, measurements are made by observing each nanoparticle present on a stage using transmission electron microscopy (TEM) and determining their number average particle size.

As nanoparticles to be formed into a water-soluble nanoparticle complex, gold nanoparticles are preferably used. In gold nanoparticles, since plasmon frequency of free electrons present on the surface falls in the frequency region of the optical electric field of the ultraviolet to near infrared region, resonance with the optical electric field causes strong plasmon oscillation (localized surface plasmon resonance). It is expected that localized surface plasmon resonance will be amplified by forming gold nanoparticles into a water-soluble nanoparticle complex, and thus the present invention can provide the application of gold nanoparticles to various optical application technologies.

Further, as nanoparticles to be formed into a water-soluble nanoparticle complex, semiconductor nanoparticles are preferably used. Semiconductor nanoparticles are particles composed of semiconductors on the order of nanometers and emit fluorescence corresponding to band-gap energies. It is known that semiconductor nanoparticles are inorganic semiconductors and therefore have high fluorescence properties such as being stable compared to organic dyes. Further, due to the phenomenon called the quantum size effect where the electronic state in a material changes with decreasing particle size and light with a shorter wavelength is absorbed or emitted, light emission at various wavelengths can be obtained by changing the particle size. Emission intensity per particle is enhanced by forming semiconductor nanoparticles into a water-soluble nanoparticle complex, and thus the present invention can provide the application of semiconductor nanoparticles as a fluorescent reagent. Semiconductor nanoparticles comprising at least a Group 12 element of the periodic table and a Group 16 element of the periodic table, comprising a Group 11 element of the periodic table, a Group 13 element of the periodic table, and a Group 16 element of the periodic table, or comprising a Group 13 element of the periodic table and a Group 15 element of the periodic table are preferably used.

The average particle size of the water-soluble nanoparticle complex is preferably 10 to 300 nm and more preferably 30 to 300 nm from the standpoint of improving the properties of nanoparticles. The average particle size of the water-soluble nanoparticle complex can be controlled by the degree of polymerization (DP) of the water-soluble polymer. The average particle size of the water-soluble nanoparticle complex is measured by the dynamic light scattering (DLS) method, which is specifically the method of measuring the light scattering intensity distribution and diffusion coefficient of a water-soluble nanoparticle complex dispersion and then analyzing/calculating the average particle size and particle size distribution of the water-soluble nanoparticle complex by the histogram method (in particular, the CUMULANT method).

Examples of specific procedures of the method for preparing the water-soluble nanoparticle complex include the following two methods.

First, a nanoparticle dispersion obtained by dispersing nanoparticles in an organic solvent is provided. Examples of the organic solvent here include pyridine, hexane, cyclohexane, methylene chloride, chloroform, tetrahydrofuran, and dimethyl sulfoxide, and chloroform is preferably used. Next, an aqueous nanoparticle solution is provided. A low molecular-weight water-solubilizer is added to the nanoparticle dispersion, and the resulting mixture is stirred at room temperature for 1 to 12 hours. Examples of low molecular-weight water-solubilizers include mercaptopropionic acid (MPA) and mercaptoethanesulfonic acid (MES), and mercaptopropionic acid (MPA) is preferably used. After the stirring, the nanoparticles are extracted into an aqueous layer using Tris buffer, and then the purification operation of acetone reprecipitation, centrifugation, and redispersion in Milli-Q water is repeated to obtain an aqueous nanoparticle solution. When the nanoparticles are gold nanoparticles, a commercially available aqueous citrate-reduced gold nanoparticle solution may be used. Then, a water-soluble polymer solution obtained by dissolving a water-soluble polymer in an aqueous solvent is provided. Examples of aqueous solvents include acetate buffer, phosphate buffer, citrate buffer, borate buffer, Tris buffer, and Milli-Q water, and Tris buffer and Milli-Q water are preferably used. The aqueous solvent for dissolving a water-soluble polymer is preferably basic, and, specifically, an aqueous solvent the pH of which is adjusted to pH 10 with barium hydroxide, sodium hydroxide, potassium hydroxide, ammonia, sodium carbonate, or sodium hydrogen carbonate is preferably used. The mixed solution of the aqueous nanoparticle solution obtained and the water-soluble polymer solution obtained is mixed by stirring at room temperature for 1 to 12 hours. Upon mixing, a ligand exchange reaction occurs between the low molecular-weight water-solubilizer at the nanoparticle surface and the water-soluble polymer to yield a water-soluble nanoparticle complex, which is a complex of a plurality of nanoparticles and a water-soluble polymer, in the mixed solution. The water-soluble nanoparticle complex yielded in the mixed solution is recovered using water dialysis and ultrafiltration by removing the free water-soluble polymer and nanoparticles.

In an alternative preparation method, a complex can be formed by reacting a water-soluble polymer dispersed in an organic solvent directly with semiconductor nanoparticles dispersed in the same organic solvent. First, nanoparticles dispersed in an organic solvent and a water-soluble polymer dispersion are separately provided. Examples of the organic solvent here include pyridine, hexane, cyclohexane, methylene chloride, chloroform, tetrahydrofuran, and dimethyl sulfoxide, and chloroform is preferably used. The mixed solution of the nanoparticle dispersion and the water-soluble polymer dispersion is mixed by stirring at room temperature for 1 to 24 hours. Upon mixing, a ligand exchange reaction occurs between a hydrophobic modifier at the nanoparticle surface and the water-soluble polymer. Next, the mixed solution is injected into a dialysis membrane, and solvent replacement is performed using as an external solution a solvent having affinity for both the organic solvent used for the mixed solution and water. Examples of the solvent here include methanol, ethanol, propanol, butanol, and 2-propanol, and methanol is preferably used. Next, solvent replacement with an aqueous solution is performed again using water as an external solution to obtain a water-soluble nanoparticle complex, which is a complex of a plurality of nanoparticles and a water-soluble polymer. The water-soluble nanoparticle complex formed in the aqueous solution is recovered using ultrafiltration by removing the free water-soluble polymer and nanoparticles.

The presence of formation of the water-soluble nanoparticle complex obtained by either of the preparation methods described above, its form, the presence of accumulated nanoparticles, and the like can be checked by transmission electron microscope (TEM), scanning transmission electron microscope (BF-STEM, HAADF-STEM), or atomic force microscope (AFM) measurements.

[Reagent]

The water-soluble nanoparticle complex described above can be widely utilized in diagnosis/prognosis of human health conditions, drug discovery, and other fields because it is applicable as a detection reagent in various technologies for detecting an interaction between substances (hereinafter referred to as "sensing technology") and can be preferably used as a reagent for detecting with high sensitivity a trace amount of biomolecules that are present in the body or produced in the body. Examples of biomolecules detected by sensing technologies include, as mentioned above, nucleic acids such as genomic DNA and RNA, proteins, peptides, saccharides, lipids, hormones, and the like.

Specifically, when detecting nucleic acids in vivo, a DNA chip in which a number of probe nucleic acids are immobilized on a substrate is known as a tool for detecting the nucleic acids, and the presence of the nucleic acids in vivo can be detected by hybridizing nucleic acids extracted from in vivo and labeled with the water-soluble nanoparticle complex described above or its copy with the probe nucleic acids on a substrate and detecting signals on the substrate deriving from the water-soluble nanoparticle complex described above. Alternatively, signals on the substrate deriving from the water-soluble nanoparticle complex described above can be detected by hybridizing unlabeled nucleic acids in vivo or its copy with the probe nucleic acids on the substrate and then binding the water-soluble nanoparticle complex described above to the nucleic acids, for example, by chemical reaction.

Also when detecting proteins in vivo, the presence of proteins in vivo can be detected using the same method as the method for detecting a nucleic acid described above by utilizing an interaction between the proteins and proteins or nucleic acids immobilized on a substrate.

EXAMPLES

Selected features will now be described more specifically with reference to Examples, but our polymers and methods are not limited to Examples. With respect to various compounds used in Examples, those that are commercially available as a reagent were used.

Example 1

Synthesis of Water-Soluble Polymer 1

(Polymer 1)
Under a dry argon atmosphere, methyl p-tosylate (4 mmol, 0.6 mL), an initiator, and monomeric 2-ethyl-2-oxazoline (EtOx) (88.4 mmol, 8.92 mL) were added into a solvent of acetonitrile (30 mL) to carry out cation ring-opening polymerization. After the reaction in a thermostat bath at 50° C. for 7 days, the resultant was cooled to room temperature, and termination reaction was carried out using 1 M sodium hydroxide/methanol mixed solvent (introduction of a hydroxyl group (—OH) into a terminal end). After purification by water dialysis, 7 g of polymer was recovered by drying under reduced pressure. The degree of polymerization and polydispersity index of the poly(2-ethyl-2-oxazoline) (PEtOx) obtained were determined by $^1$H-NMR spectrum and GPC diagram, respectively (Degree of polymerization (DP)=22, Polydispersity index (PDI: Mw/Mn)=1.1).

To obtain a linear polyethyleneimine (PEI) by side chain degradation reaction, PEtOx (3 g) was dissolved in a mixed solvent of 37% hydrochloric acid (30 mL) and water (24 mL) and the resultant was refluxed at about 110° C. for 24 hours. Sodium hydroxide pellets were inserted into the reaction solution until it became completely clear to adjust to a pH of 9 to 10, and then 1.2 g of PEI was recovered by water dialysis and lyophilization. Measurements of the obtained polymer by $^1$H-NMR confirmed that the side chain degradation reaction was quantitatively carried out because hydrogen-derived peaks of the backbone and side chain of PEtOx all disappeared and methylene hydrogen-derived peaks of ethyleneimine (—NHCH$_2$CH$_2$—) of the PEI backbone were present at about 3.2 to 3.4 ppm.

Figure 2:
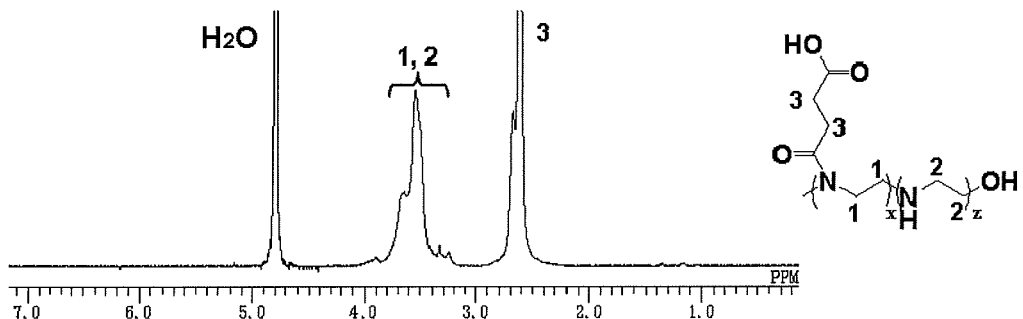
FIG. 2 is a drawing for explaining the $^1$H-NMR spectrum of mPEI-COOH (x=99%)-EI (z=1%), a synthetic intermediate of Polymer 1.

Next, succinic anhydride (14.0 mmol, 1.4 g) and pyridine (0.5 mL) were added into a mixed solvent of PEI (0.53 mmol, 500 mg) in water (2.5 mL)/acetonitrile (2.5 mL), and the resultant was allowed to react for 12 hours with stirring at room temperature, after which ethanol dialysis and water dialysis were sequentially performed. After the dialyses, mPEI-COOH (1.1 g) into the side chain of which carboxyl groups were introduced was obtained by lyophilization. Each component of the polymer obtained was able to be assigned each from methylene hydrogens (1, 2) of the ethyleneimine backbone (—NHCH$_2$CH$_2$—) and methylene hydrogens (3) of the carboxyl group of the side chain in $^1$H-NMR spectrum (FIG. 2, $^1$H-NMR spectrum shows that the carboxyl group introduction rate into the side chain is 99%).

Figure 3:
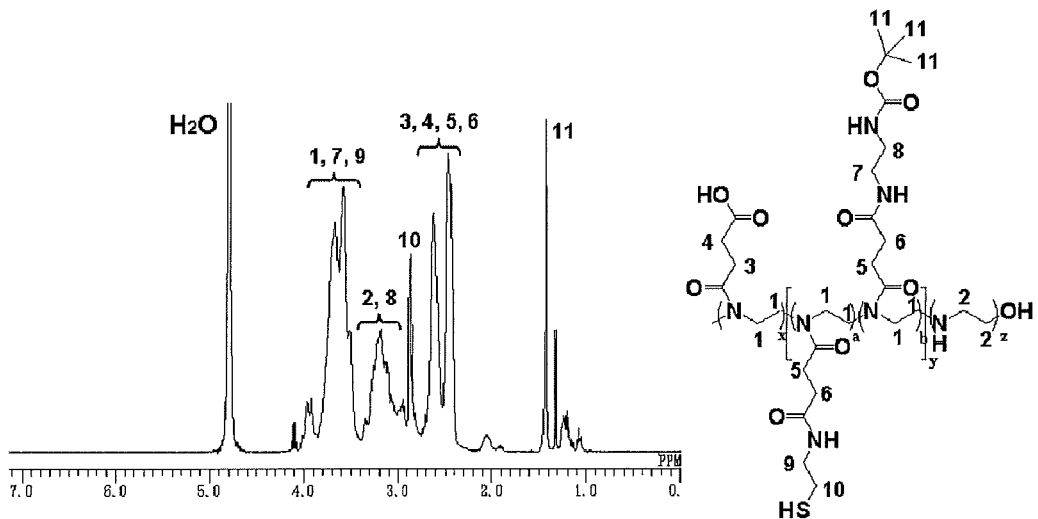
FIG. 3 is a drawing for explaining the $^1$H-NMR spectrum of mPEI-COOH (x)-[SH (a)-NH-Boc (b)] (y)-EI (z), a synthetic intermediate of Polymer 1.

Thereafter, N-Boc-ethylenediamine (0.117 mmol, 18.7 mg), cysteamine (0.117 mmol, 9 mg), and 1-ethyl-3-(3-dimethylaminopropyl)carbodiimide (EDAC) (0.4 mmol, 77 mg) were inserted into an aqueous solution (1 mL) of mPEI-COOH-EI (50 mg), and the resultant was allowed to react at room temperature for 12 hours, after which 70 mg of polymer was recovered by water dialysis and lyophilization. Each component of the polymer obtained was able to be assigned each from methylene hydrogens (1, 2) of the ethyleneimine backbone (—NHCH$_2$CH$_2$—), methylene hydrogens (3, 4, 5, 6, 7, 8, 9, 10) of the side chain, and methyl hydrogens (11) of the N-Boc protecting group in $^1$H-NMR spectrum (FIG. 3).

Figure 4:
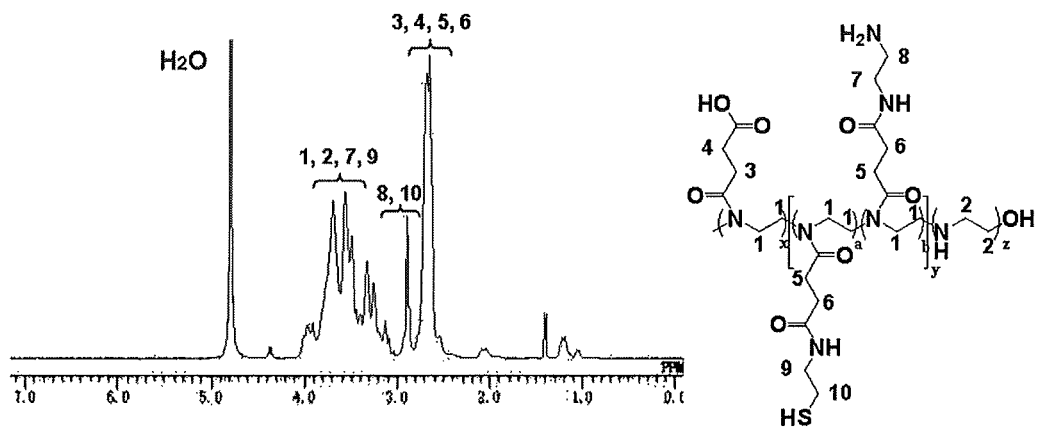
FIG. 4 is a drawing for explaining the $^1$H-NMR spectrum of mPEI-COOH (x)-[SH (a)-NH$_2$ (b)] (y)-EI (z), Polymer 1.

Then, 2 mL of trifluoroacetic acid (TFA) was inserted into the polymer obtained (70 mg) to carry out the deprotection reaction of the N-Boc protecting group, confirming that the peak derived from methyl hydrogens of the N-Boc protecting group (11 in FIG. 3) disappeared (FIG. 4). The composition ratio of the polymer backbone and each segment was calculated from the integral ratio of $^1$H-NMR spectrum to confirm mPEI-COOH (x)-[SH (a)-NH$_2$ (b)] (y)-EI (z)(x/(x+y+z)= 0.40, y/(x+y+z)=0.59 [a=0.34, b=0.25], and z/(x+y+z)=0.01) (FIG. 4, Yield: 40 mg, Polymer 1).

Example 2

Synthesis of Water-Soluble Polymer 2

For those having a segment composition ratio different from that of the water-soluble polymer obtained in Example 1, the same synthesis operation as in Example 1 was carried out. The composition of the water-soluble polymer obtained was as shown below.
(Polymer 2)
[Synthesis Conditions and Results of PEtOx]
Loading amount: acetonitrile (36 mL), methyl p-tosylate (0.3 mmol, 0.045 mL), EtOx (96 mmol, 9.7 mL), Yield: 7 g, Degree of polymerization (DP)=302, Polydispersity index (PDI: Mw/Mn)=1.1)
[Synthesis Conditions and Results of PEI]
Loading amount: PEtOx (3 g), 37% hydrochloric acid (30 mL)/water (24 mL), Yield: 1.2 g
[Synthesis Conditions and Results of mPEI-COOH-EI]
Loading amount: PEI (0.038 mmol, 500 mg), water (2.5 mL)/acetonitrile (2.5 mL), succinic anhydride (13.8 mmol, 1.38 g), pyridine (0.5 mL), Yield: 1.6 g
[Synthesis Conditions and Results of mPEI-COOH—SH—NH$_2$-EI]
Loading amount: mPEI-COOH (150 mg), water (2 mL), N-Boc-ethylenediamine (0.3 mmol, 48.3 mg), cysteamine (0.3 mmol, 23.3 mg), EDAC (0.76 mmol, 145.7 mg). After the deprotection reaction using TFA, the composition ratio of each segment of the water-soluble polymer calculated from the integral value ratio of $^1$H-NMR spectrum was mPEI-COOH (x)-[SH (a)-NH$_2$ (b)] (y)-EI (z) (x/(x+y+z)=0.40, y/(x+y+z)=0.58 [a=0.30, b=0.28], and z/(x+y+z)=0.02) (Yield: 160 mg, Polymer 2).
(Polymer 3)
[Synthesis Conditions and Results of PEtOx]
Loading amount: acetonitrile (30 mL), methyl p-tosylate (2 mmol, 0.3 mL), EtOx (88.4 mmol, 8.92 mL), Yield: 8 g, Degree of polymerization (DP)=43, Polydispersity index (PDI: Mw/Mn)=1.08)
[Synthesis Conditions and Results of PEI]
Loading amount: PEtOx (3 g), 37% hydrochloric acid (30 mL)/water (24 mL), Yield: 1.1 g
[Synthesis Conditions and Results of mPEI-COOH-EI]
Loading amount: PEI (0.26 mmol, 500 mg), water (2.5 mL)/acetonitrile (2.5 mL), succinic anhydride (8.9 mmol, 890 mg), pyridine (0.3 mL), Yield: 1.3 g
[Synthesis Conditions and Results of mPEI-COOH—SH—NH$_2$-EI]
Loading amount: mPEI-COOH (100 mg), water (2 mL), N-Boc-ethylenediamine (0.27 mmol, 42.6 mg), cysteamine (0.27 mmol, 20.5 mg), EDAC (0.67 mmol, 127.5 mg). After the deprotection reaction using TFA, the composition ratio of each segment of the water-soluble polymer calculated from the integral value ratio of $^1$H-NMR spectrum was mPEI-COOH (x)-[SH (a)-NH$_2$ (b)] (y)-EI (z) (x/(x+y+z)=0.27, y/(x+y+z)=0.55 [a=0.27, b=0.28], and z/(x+y+z)=0.18) (Yield: 140 mg, Polymer 3).

(Polymer 4)

[Synthesis Conditions and Results of PEtOx]

Loading amount: acetonitrile (30 mL), methyl p-tosylate (2 mmol, 0.3 mL), EtOx (88.4 mmol, 8.92 mL), Yield: 8 g, Degree of polymerization (DP)=43, Polydispersity index (PDI: Mw/Mn)=1.08)

[Synthesis Conditions and Results of PEI]

Loading amount: PEtOx (3 g), 37% hydrochloric acid (30 mL)/water (24 mL), Yield: 1.1 g

[Synthesis Conditions and Results of mPEI-COOH-EI]

Loading amount: PEI (0.26 mmol, 500 mg), water (2.5 mL)/acetonitrile (2.5 mL), succinic anhydride (8.9 mmol, 890 mg), pyridine (0.3 mL), Yield: 1.3 g

[Synthesis Conditions and Results of mPEI-COOH—SH-EI]

Figure 5:
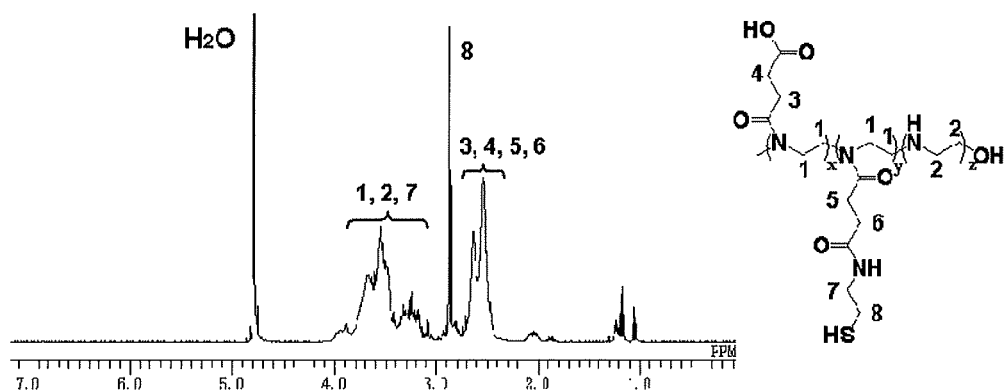
FIG. 5 is a drawing for explaining the $^1$H-NMR spectrum of mPEI-COOH (x)-SH (y)-EI (z), Polymer 4.

Loading amount: mPEI-COOH (25 mg), water (1 mL), cysteamine (0.097 mmol, 7.5 mg), EDAC (0.0978 mmol, 18.75 mg). The composition ratio of each segment of the water-soluble polymer calculated from the integral value ratio of $^1$H-NMR spectrum was mPEI-COOH (x)-SH (y)-EI (z) (x/(x+y+z)=0.50, y/(x+y+z)=0.32, z/(x+y+z)=0.18) (FIG. 5, Yield: 30 mg, Polymer 4).

(Polymer 5)

[Synthesis Conditions and Results of PEtOx]

Loading amount: acetonitrile (30 mL), methyl p-tosylate (1 mmol, 0.15 mL), EtOx (88.4 mmol, 8.92 mL), Yield: 8 g, Degree of polymerization (DP)=93, Polydispersity index (PDI: Mw/Mn)=1.1)

[Synthesis Conditions and Results of PEI]

Loading amount: PEtOx (3 g), 37% hydrochloric acid (30 mL)/water (24 mL), Yield: 1.2 g

[Synthesis Conditions and Results of mPEI-COOH-EI]

Loading amount: PEI (0.025 mmol, 100 mg), water (2 mL)/acetonitrile (1 mL), succinic anhydride (2.1 mmol, 210 mg), pyridine (0.3 mL), Yield: 280 mg

[Synthesis Conditions and Results of mPEI-COOH—SH-EI]

Loading amount: mPEI-COOH (40 mg), water (1 mL), cysteamine (0.097 mmol, 7.5 mg), EDAC (0.0978 mmol, 18.75 mg). The composition ratio of each segment of the water-soluble polymer calculated from the integral value ratio of $^1$H-NMR spectrum was mPEI-COOH (x)-SH (y)-EI (z) (x/(x+y+z)=0.66, y/(x+y+z)=0.22, z/(x+y+z)=0.12) (Yield: 45 mg, Polymer 5).

Example 3

Synthesis of Water-Soluble Polymer 3

The side chain modification reaction was similar to those of the water-soluble polymer obtained in Examples 1 and 2, but, for those polymers in which a biotin ligand was introduced into the terminal end of the water-soluble polymer, the synthesis operation as described below was performed.

(Polymer 6)

Under a dry argon atmosphere, methyl p-tosylate (1 mmol, 0.15 mL) and EtOx (88.4 mmol, 8.92 mL) were added into a solvent of acetonitrile (30 mL) to carry out cation ring-opening polymerization. After the reaction in a thermostat bath at 50° C. for 7 days, the resultant was cooled to room temperature, and 4-(N-Boc-amino)piperidine (5 mmol, 1 g) was inserted thereinto as a terminator, after which termination reaction was carried out in a thermostat bath at 50° C. for 1 day. After purification by water dialysis, 8 g of polymer was recovered by drying under reduced pressure. The degree of polymerization of the polymer obtained (PEtOx) and the N-Boc-amino group introduction rate into the terminal end were confirmed by $^1$H-NMR spectrum (Degree of polymerization (DP)=93, Introduction rate=86%).

Simultaneously with the introduction of a primary amino group (—NH$_2$) by deprotection reaction of the terminal end Boc, to obtain linear PEI by side chain degradation reaction, PEtOx (3 g) was dissolved in a mixed solvent of 37% hydrochloric acid (30 mL) and water (24 mL), and the resultant was refluxed at about 110° C. for 24 hours. Sodium hydroxide pellets were inserted into the reaction solution until it became completely clear to adjust to a pH of 9 to 10, and then 1.2 g of polymer was recovered by water dialysis and lyophilization. Measurements of the obtained polymer by $^1$H-NMR confirmed that hydrogen-derived peaks of the backbone and side chain of PEtOx all disappeared; methylene hydrogen-derived peaks of ethyleneimine (—NHCH$_2$CH$_2$—) of the PEI backbone were present at about 3.2 to 3.4 ppm; and peaks derived from methyl hydrogens of the N-Boc protecting group at the PEtOx terminal end disappeared.

Figure 6:
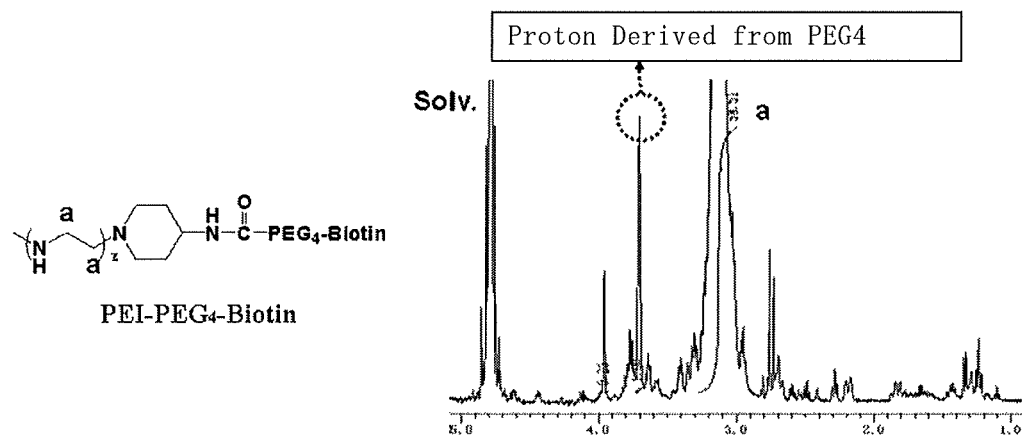
FIG. 6 is a drawing for explaining the $^1$H-NMR spectrum of Biotin-PEG4-PEI, a synthetic intermediate of Polymer 6.

Then, NHS-PEG$_4$-Biotin (0.023 mmol, 13.5 mg) was added into a mixed solvent of PEI having a primary amino group at the terminal end (0.023 mmol, 100 mg) in water (1 mL)/DMSO (2 mL), and the resultant was allowed to react for 24 hours with stirring at room temperature, after which ethanol dialysis and water dialysis were sequentially performed. After the dialyses, Biotin-PEG$_4$-PEI into the terminal end of which Biotin was introduced via a PEG$_4$ spacer was recovered (Yield: 82.5 mg) by lyophilization. The terminal biotin introduction rate of the polymer obtained was able to be calculated from methylene hydrogens (a) of the ethyleneimine backbone (—NHCH$_2$CH$_2$—) and methylene hydrogens of the ethylene oxide backbone (—(OCH$_2$CH$_2$)$_{1-4}$—) in $^1$H-NMR spectrum (FIG. 6, Biotin introduction rate is 60%).

Figure 7:
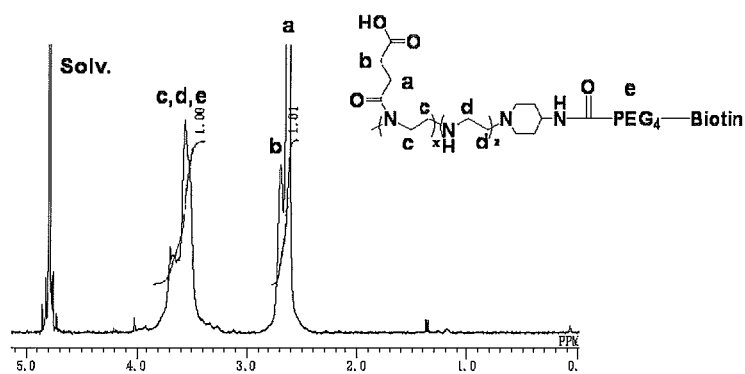
FIG. 7 is a drawing for explaining the $^1$H-NMR spectrum of Biotin-PEG4-mPEI-COOH-EI, a synthetic intermediate of Polymer 6.

Thereafter, succinic anhydride (10.0 mmol, 1 g) and pyridine (1 mL) were added into a mixed solvent of Biotin-PEG$_4$-PEI (82.5 mg) in water (2 mL)/acetonitrile (1 mL), and the resultant was allowed to react for 12 hours with stirring at room temperature, after which ethanol dialysis and water dialysis were sequentially performed. After the dialyses, Biotin-PEG$_4$-mPEI-COOH-EI (126.2 mg) into the side chain of which carboxyl groups were introduced was obtained by lyophilization. Each component of the polymer obtained was able to be assigned each from methylene hydrogens (1, 2) of the ethyleneimine backbone (—NHCH$_2$CH$_2$—) and methylene hydrogens (3) of the carboxyl group of the side chain in $^1$H-NMR spectrum (FIG. 7, $^1$H-NMR spectrum shows that the carboxyl group introduction rate into the side chain is 99%).

Figure 8:
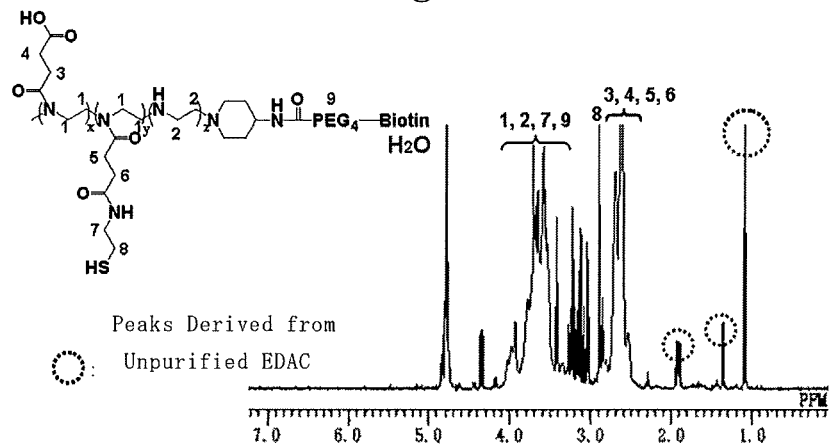
FIG. 8 is a drawing for explaining the $^1$H-NMR spectrum of mBiotin-PEG4-mPEI-COOH (x)-SH (y)-EI (z), Polymer 6.

Finally, cysteamine (0.165 mmol, 12.7 mg) and EDAC (0.165 mmol, 31.6 mg) were inserted into an aqueous solution (0.5 mL) of Biotin-PEG$_4$-mPEI-COOH-EI (50 mg), and the resultant was allowed to react at room temperature for 12 hours, after which 55 mg of polymer was recovered by water dialysis and lyophilization. The composition ratio of each segment of the water-soluble polymer calculated from the integral value ratio of $^1$H-NMR spectrum was confirmed to be Biotin-PEG$_4$-mPEI-COOH (x)-SH (y)-EI (z) (x/(x+y+z)=0.44, y/(x+y+z)=0.44, z/(x+y+z)=0.12) (FIG. 8, Polymer 6).

(Polymer 7)

[Synthesis Conditions and Results of PEtOx]

Loading amount: acetonitrile (30 mL), methyl p-tosylate (1 mmol, 0.15 mL), EtOx (88.4 mmol, 8.92 mL), 4-(N-Bocamino)piperidine (5 mmol, 1 g), Yield: 8 g, Degree of polymerization (DP)=93, Polydispersity index (PDI: Mw/Mn)=1.1)

[Synthesis Conditions and Results of PEI]

Loading amount: PEtOx (3 g), 37% hydrochloric acid (30 mL)/water (24 mL), Yield: 1.2 g

[Synthesis Conditions and Results of Biotin-$PEG_{113}$-PEI]

Loading amount: PEI having a primary amino group at the terminal end (0.03 mmol, 120 mg), water (2 mL), NHS-$PEG_{113}$-Biotin (0.02 mmol, 100 mg), Yield: 200 mg

[Synthesis Conditions and Results of Biotin-$PEG_{113}$-mPEI-COOH-EI]

Loading amount: Biotin-$PEG_{113}$-PEI (200 mg), water (2 mL)/acetonitrile (1 mL), succinic anhydride (2.5 mmol, 250 mg), pyridine (0.4 mL), Yield: 400 mg

[Synthesis Conditions and Results of Biotin-$PEG_{113}$-mPEI-COOH—SH-EI]

Loading amount: Biotin-$PEG_{113}$-mPEI-COOH-EI (100 mg), water (1 mL), cysteamine (0.7 mmol, 54 mg), EDAC (0.7 mmol, 134 mg). The composition ratio of each segment of the water-soluble polymer calculated from the integral value ratio of $^1$H-NMR spectrum was Biotin-$PEG_{113}$-mPEI-COOH (x)-SH (y)-EI (z) (x/(x+y+z)=0.55, y/(x+y+z)=0.43, z/(x+y+z)=0.02) (Yield: 145 mg, Polymer 7).

Example 4

Synthesis of Water-Soluble Polymer 4

The side chain modification reaction was similar to those of the water-soluble polymer obtained in Examples 1 and 2, but, for those polymers in which a primary amino group (functional group capable of binding to a complex surface ligand) was introduced into the terminal end of the water-soluble polymer, the synthesis operation as described below was performed.

(Polymer 8)

Under a dry argon atmosphere, methyl p-tosylate (8 mmol, 1.2 mL) and EtOx (176.8 mmol, 17.84 mL) were added into a solvent of acetonitrile (50 mL) to carry out cation ring-opening polymerization. After the reaction in a thermostat bath at 49° C. for 5 days, the resultant was cooled to room temperature, 4-(N-Boc-amino)piperidine (16 mmol, 3.2 g) was inserted thereinto as a terminator, after which termination reaction was carried out in a thermostat bath at 49° C. for 2 days. After purification by water dialysis, 7 g of polymer was recovered by drying under reduced pressure. The degree of polymerization of the polymer obtained (PEtOx) and the N-Boc-amino group introduction rate into the terminal end were confirmed by $^1$H-NMR spectrum (Degree of polymerization (DP)=24, Introduction rate=100%).

Simultaneously with the introduction of a primary amino group ($-NH_2$) by deprotection reaction of the terminal end Boc, to obtain linear PEI by side chain degradation reaction, PEtOx (7 g) was dissolved in a mixed solvent of 37% hydrochloric acid (70 mL) and water (56 mL), and the resultant was refluxed at about 110° C. for 24 hours. NaOH pellets were inserted into the reaction solution until it became completely clear to adjust to a pH of 9 to 10, and then 2.5 g of polymer was recovered by water dialysis and lyophilization. Measurements of the obtained polymer by $^1$H-NMR confirmed that hydrogen-derived peaks of the backbone and side chain of PEtOx all disappeared; methylene hydrogen-derived peaks of ethyleneimine ($-NHCH_2CH_2-$) of the PEI backbone were present at about 3.2 to 3.4 ppm; and peaks deriving from methyl hydrogens of the N-Boc protecting group at the PEtOx terminal end disappeared.

Figure 9:
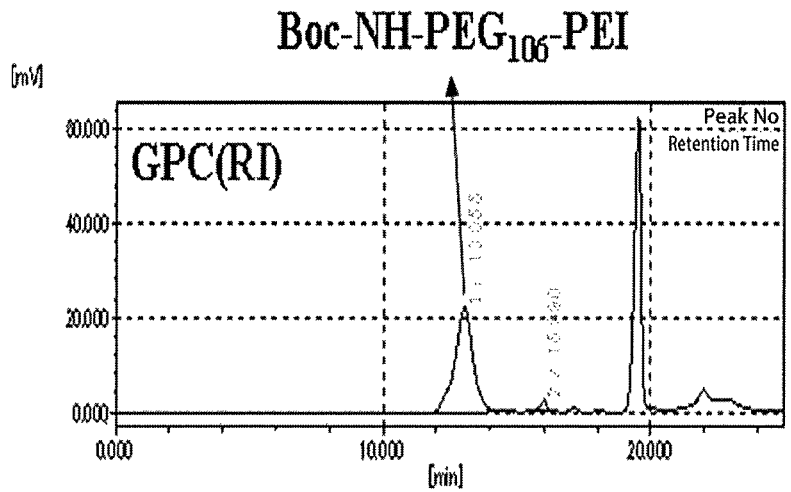
FIG. 9 is a drawing for explaining the GPC diagram of Boc-NH-PEG$_{106}$-PEI, a synthetic intermediate of Polymer 8.

Next, PEI having a primary amino group at the terminal end (0.2 mmol, 226.8 mg) was dissolved in ultrapure water (3 mL). Further, polyethylene glycol having a Boc-protected primary amino group and an active ester group at both ends (Boc-NH-$PEG_{106}$-NHS) (BO-050TS available from NOF CORPORATION, MW=4670) (0.2 mmol, 1 g) was poured into ultrapure water (4 mL) and dissolved. Then, both aqueous polymer solutions were mixed, and the resultant was allowed to react for 48 hours with stirring at room temperature, after which water dialysis and ion-exchange chromatographic purification were sequentially performed. Thereafter, Boc-NH-$PEG_{106}$-PEI into the terminal end of which a protected primary amino group was introduced via a $PEG_{106}$ spacer was recovered (Yield: 500 mg) by lyophilization. The results of the synthesis of the polymer obtained were confirmed by the aqueous GPC (high-performance GPC system "HLC-8320 GPC EcoSEC" available from TOSOH CORPORATION, TSKgel G3000PWXL-CP, TSK guard column) measurements (FIG. 9).

Figure 10:
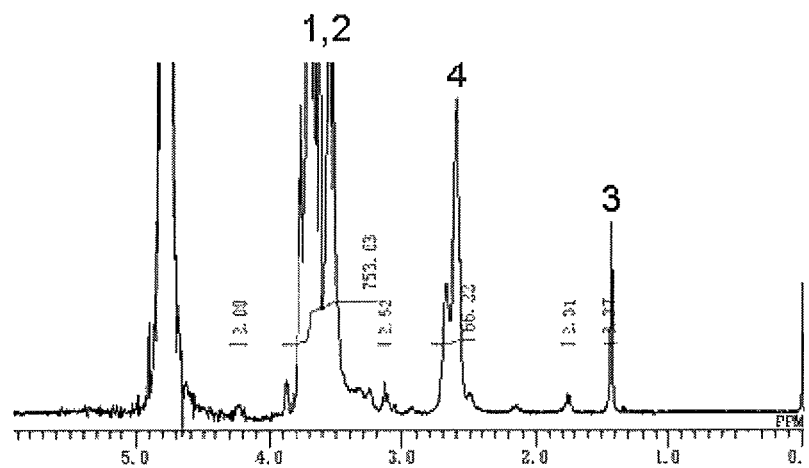
FIG. 10 is a drawing for explaining the $^1$H-NMR spectrum of Boc-NH-PEG$_{106}$-PEI, a synthetic intermediate of Polymer 8.

Thereafter, a solution of succinic anhydride (807 mg) in acetonitrile (6 mL) and pyridine (0.425 mL) were added into an aqueous solution (8 mL) of Boc-NH-$PEG_{106}$-PEI (650 mg), and the resultant was allowed to react for 24 hours with stirring at room temperature, after which ethanol dialysis and water dialysis were sequentially performed. After the dialyses, Boc-NH-$PEG_{106}$-mPEI-COOH-EI (730 mg) into the side chain of which carboxyl groups were introduced was obtained by lyophilization. Each component of the polymer obtained was able to be assigned each from methylene hydrogens (1, 2) deriving from the ethyleneimine backbone ($-NHCH_2CH_2-$) and the ethylene glycol backbone ($-OCH_2CH_2-$), methylene hydrogens (4) deriving from the carboxyl group of the ethyleneimine side chain, and methyl hydrogens (3) deriving from the Boc protecting group in $^1$H-NMR spectrum (FIG. 10, $^1$H-NMR spectrum shows that the carboxyl group introduction rate into the side chain is 67%).

Next, pyridyl disulfide cysteamine hydrochloride (CASSPy) (1.444 g)/0.1 M $NaHCO_3$ buffer (pH 8.4) (10 mL) and EDAC (1.243 g)/0.1 M $NaHCO_3$ buffer (pH 8.4) (10 mL) were inserted into a 0.1 M $NaHCO_3$ buffer (pH 8.4) (20 mL) of Boc-NH-$PEG_{106}$-mPEI-COOH-EI (200 mg), and the resultant was allowed to react at room temperature for 12 hours, after which 257.4 mg of polymer was recovered by ultrafiltration and lyophilization. It was confirmed that a primary amino group ($-NH_2$) was successfully introduced from a $PEG_{106}$ end Boc-NH— by trifluoroacetic acid (TFA) deprotection reaction and that quantitative deprotection was achieved by reacting protecting SH groups of the polymer side chain with three times the amount of a reducing agent (dithiothreitol, DTT) in water. The composition ratio of each segment of the water-soluble polymer calculated from the integral value ratio of $^1$H-NMR spectrum was confirmed to be Boc-NH-$PEG_{106}$-mPEI-COOH (x)-SH (y)-EI (z) (x/(x+y+z)= 0.04, y/(x+y+z)=0.63, z/(x+y+z)=0.33) (Polymer 8).

(Polymer 9)

Synthesis Conditions and Results of PEtOx

Loading amount: acetonitrile (50 mL), methyl p-tosylate (8 mmol, 1.2 mL), EtOx (176.8 mmol, 17.84 mL), 4-(N-Boc-amino)piperidine (16 mmol, 3.2 g), Yield: 7 g, Degree of polymerization (DP)=24

Synthesis Conditions and Results of PEI

Loading amount: PEtOx (7 g), 37% hydrochloric acid (70 mL)/water (56 mL), Yield: 2.5 g Synthesis Conditions and Results of Boc-NH-$PEG_{51}$-PEI Loading amount: PEI having a primary amino group at the terminal end (0.44 mmol, 500 mg)/water (4 mL), Boc-NH- PEG$_{51}$-NHS (0.44 mmol, 1 g)/water (4 mL), Yield: 1.024 g
Synthesis Conditions and Results of Boc-NH-PEG$_{51}$-mPEI-COOH-EI
 Loading amount: Boc-NH-PEG$_{51}$-PEI (410 mg)/water (2 mL), succinic anhydride (864.6 mg)/acetonitrile (5 mL), pyridine (0.228 mL), Yield: 480 mg
Synthesis Conditions and Results of Boc-NH-PEG$_{51}$-mPEI-COOH—SH-EI
 Loading amount: Boc-NH-PEG$_{51}$-mPEI-COOH-EI (200 mg), water (3 mL), cysteamine (231.5 mg), EDAC (575.13 mg). The composition ratio of each segment of the water-soluble polymer calculated from the integral value ratio of $^1$H-NMR spectrum was Boc-NH-PEG$_{51}$-mPEI-COOH (x)-SH (y)-EI (z) (x/(x+y+z)=0.11, y/(x+y+z)=0.24, z/(x+y+z)=0.65) (Yield: 275 mg, Polymer 9).

Example 5

Synthesis of Water-Soluble Polymer 5

The side chain modification reaction was similar to those performed in Examples 1 and 2, but, for the other polymer composition, the synthesis operation as described below was performed.
(Polymer 10)
Synthesis Conditions and Results of PEtOx
 Loading amount: acetonitrile (30 mL), methyl p-tosylate (1 mmol, 0.15 mL), EtOx (88.4 mmol, 8.92 mL), Yield: 8 g, Degree of polymerization (DP)=93, Polydispersity index (PDI: Mw/Mn)=1.1)
Synthesis Conditions and Results of PEI
 Loading amount: PEtOx (3 g), 37% hydrochloric acid (30 mL)/water (24 mL) (Yield: 1.2 g, Polymer 10).
(Polymer 11)
Synthesis Conditions and Results of PEtOx
 Loading amount: acetonitrile (36 mL), methyl p-tosylate (0.3 mmol, 0.045 mL), EtOx (96 mmol, 9.7 mL), Yield: 7 g, Degree of polymerization (DP)=302, Polydispersity index (PDI: Mw/Mn)=1.1)
Synthesis Conditions and Results of PEI
 Loading amount: PEtOx (3 g), 37% hydrochloric acid (30 mL)/water (24 mL), Yield: 1.2 g
Synthesis Conditions and Results of mPEI-COOH-EI
 Loading amount: PEI (0.038 mmol, 500 mg), water (2.5 mL)/acetonitrile (2.5 mL), succinic anhydride (13.8 mmol, 1.38 g), pyridine (0.5 mL), and the composition ratio of each segment of the water-soluble polymer calculated from the integral value ratio of $^1$H-NMR spectrum was mPEI-COOH (x)-EI (z) (x/(x+y+z)=0.98 and z/(x+y+z)=0.02) (Yield: 1.6 g, Polymer 11).
(Polymer 12)
Synthesis Conditions and Results of PEtOx
 Loading amount: acetonitrile (30 mL), methyl p-tosylate (2 mmol, 0.3 mL), EtOx (88.4 mmol, 8.92 mL), Yield: 8 g, Degree of polymerization (DP)=43, Polydispersity index (PDI: Mw/Mn)=1.08)
Synthesis Conditions and Results of PEI
 Loading amount: PEtOx (3 g), 37% hydrochloric acid (30 mL)/water (24 mL), Yield: 1.1 g
Synthesis Conditions and Results of mPEI-COOH-EI
 Loading amount: PEI (0.26 mmol, 500 mg), water (2.5 mL)/acetonitrile (2.5 mL), succinic anhydride (8.9 mmol, 890 mg), pyridine (0.3 mL), and the composition ratio of each segment of the water-soluble polymer calculated from the integral value ratio of $^1$H-NMR spectrum was mPEI-COOH (x)-EI (z) (x/(x+y+z)=0.82, z/(x+y+z)=0.18) (Yield: 1.3 g, Polymer 12).
(Polymer 13)
Synthesis Conditions and Results of PEtOx
 Loading amount: acetonitrile (30 mL), methyl p-tosylate (4 mmol, 0.6 mL), EtOx (88.4 mmol, 8.92 mL), Yield: 7 g, Degree of polymerization (DP)=22, Polydispersity index (PDI: Mw/Mn)=1.1)
Synthesis Conditions and Results of PEI
 Loading amount: PEtOx (3 g), 37% hydrochloric acid (30 mL)/water (24 mL), Yield: 1.2 g
Synthesis Conditions and Results of mPEI-COOH-EI
 Loading amount: PEI (0.53 mmol, 500 mg), water (2.5 mL)/acetonitrile (2.5 mL), succinic anhydride (14.0 mmol, 1.4 g), pyridine (0.5 mL), and the composition ratio of each segment of the water-soluble polymer calculated from the integral value ratio of $^1$H-NMR spectrum was mPEI-COOH (x)-EI (z) (x/(x+y+z)=0.99 and z/(x+y+z)=0.01) (Yield: 1.1 g, Polymer 13).
(Polymer 14)
Synthesis Conditions and Results of PEtOx
 Loading amount: acetonitrile (30 mL), methyl p-tosylate (1 mmol, 0.15 mL), EtOx (88.4 mmol, 8.92 mL), 4-(N-Boc-amino)piperidine (5 mmol, 1 g), Yield: 8 g, Degree of polymerization (DP)=93, Polydispersity index (PDI: Mw/Mn)=1.1)
Synthesis Conditions and Results of PEI
 Loading amount: PEtOx (3 g), 37% hydrochloric acid (30 mL)/water (24 mL), Yield: 1.2 g
Synthesis Conditions and Results of mPEI-COOH—NH$_2$-EI
 Loading amount: mPEI-COOH (100 mg), water (2 mL), N-Boc-ethylenediamine (1.08 mmol, 170.4 mg), EDAC (1.34 mmol, 255 mg). After the deprotection reaction using TFA, the composition ratio of each segment of the water-soluble polymer calculated from the integral value ratio of $^1$H-NMR spectrum was mPEI-COOH (x)-NH$_2$(y)-EI (z) (x/(x+y+z)=0, y/(x+y+z)=0.98 and z/(x+y+z)=0.02) (Yield: 190 mg, Polymer 14).
(Polymer 15)
Synthesis Conditions and Results of PEtOx
 Loading amount: acetonitrile (30 mL), methyl p-tosylate (4 mmol, 0.6 mL), EtOx (88.4 mmol, 8.92 mL), Yield: 7 g, Degree of polymerization (DP)=22, Polydispersity index (PDI: Mw/Mn)=1.1)
Synthesis Conditions and Results of PEI
 Loading amount: PEtOx (3 g), 37% hydrochloric acid (30 mL)/water (24 mL), Yield: 1.2 g
Synthesis Conditions and Results of mPEI-COOH—SH-EI
 Loading amount: mPEI-COOH (50 mg), water (1 mL), cysteamine (0.468 mmol, 36 mg), EDAC (0.8 mmol, 154 mg). The composition ratio of each segment of the water-soluble polymer calculated from the integral value ratio of $^1$H-NMR spectrum was mPEI-COOH (x)-SH (y)-EI (z) (x/(x+y+z)=0, y/(x+y+z)=0.99 and z/(x+y+z)=0.01) (Yield: 70 mg, Polymer 15).
(Polymer 16)
Synthesis Conditions and Results of PEtOx
 Loading amount: acetonitrile (30 mL), methyl p-tosylate (4 mmol, 0.6 mL), EtOx (88.4 mmol, 8.92 mL), Yield: 7 g, Degree of polymerization (DP)=22, Polydispersity index (PDI: Mw/Mn)=1.1)
Synthesis Conditions and Results of PEI
 Loading amount: PEtOx (3 g), 37% hydrochloric acid (30 mL)/water (24 mL), Yield: 1.2 g
Synthesis Conditions and Results of mPEI-COOH—NH$_2$-EI
 Loading amount: mPEI-COOH (50 mg), water (1 mL), N-Boc-ethylenediamine (0.468 mmol, 74.8 mg), EDAC (0.8 mmol, 154 mg). After the deprotection reaction using TFA, the composition ratio of each segment of the water-soluble polymer calculated from the integral value ratio of $^1$H-NMR spectrum was mPEI-COOH (x)-NH$_2$(y)-EI (z) (x/(x+y+z)=0, y/(x+y+z)=0.99 and z/(x+y+z)=0.01) (Yield: 100 mg, Polymer 16).

(Polymer 17)

Synthesis Conditions and Results of PEtOx

Loading amount: acetonitrile (36 mL), methyl p-tosylate (0.3 mmol, 0.045 mL), EtOx (96 mmol, 9.7 mL), Yield: 7 g, Degree of polymerization (DP)=302, Polydispersity index (PDI: Mw/Mn)=1.1)

Synthesis Conditions and Results of PEI

Loading amount: PEtOx (3 g), 37% hydrochloric acid (30 mL)/water (24 mL), Yield: 1.2 g Synthesis Conditions and Results of mPEI-COOH-EI Loading amount: PEI (0.038 mmol, 500 mg), water (2.5 mL)/acetonitrile (2.5 mL), succinic anhydride (13.8 mmol, 1.38 g), pyridine (0.5 mL), Yield: 1.6 g Synthesis Conditions and Results of mPEI-COOH—NH$_2$-EI Loading amount: mPEI-COOH (150 mg), water (2 mL), N-Boc-ethylenediamine (1.2 mmol, 193.2 mg), EDAC (1.52 mmol, 291.4 mg). After the deprotection reaction using TFA, the composition ratio of each segment of the water-soluble polymer calculated from the integral value ratio of $^1$H-NMR spectrum was mPEI-COOH (x)-NH$_2$(y)-EI (z) (x/(x+y+z)=0, y/(x+y+z)=0.98 and z/(x+y+z)=0.02) (Yield: 250 mg, Polymer 17).

Example 6

Preparation of Water-Soluble Nanoparticle Complex (Preparation of Semiconductor Nanoparticles)

To an aqueous solution (metal ion concentration: 0.1 mol·dm$^3$) containing Zn(NO$_3$)$_2$, In(NO$_3$)$_3$, and AgNO$_3$ at a ratio of (1-2x):x:x (in this case, synthesized at x=0.2), 0.1 mol·dm$^{-3}$ of sodium N,N-diethyldithiocarbamate aqueous solution was added to obtain a precipitate of diethyldithiocarbamate (Zn$_{(1-2x)}$In$_x$Ag$_x$(S$_2$CN(C$_2$H$_5$)$_2$)$_2$, hereinafter referred to as a starting coordination compound). The coordination compound obtained was washed with water, further washed with methanol, and then dried under reduced pressure to a powder. The powder in an amount of 50 mg and a magnetic stirrer bar were placed into a test tube, which was sealed with a septum cap, and the inside was purged with argon gas. Then, using an oil bath, the test tube was heated at 180° C. for 3 minutes with stirring to thereby pyrolyze the coordination compound. After cooling to room temperature and adding 3 mL of oleylamine as alkylamine under an argon atmosphere, again using the oil bath, the test tube was heated at 180° C. for 3 minutes with stirring. After cooling to room temperature, supernatant was recovered by centrifugation. It appears that, in this supernatant, semiconductor nanoparticles modified with oleylamine are dispersed using the oleylamine itself as a solvent. An equivalent amount of methanol was added thereto to precipitate the semiconductor nanoparticles, and the operation of removing an excess of oleylamine by centrifugation was repeated three times. The solid obtained was dispersed in chloroform to prepare a chloroform solution of oleylamine-modified semiconductor nanoparticles (ZnAgInS).

(Water-Solubilization of Semiconductor Nanoparticles with Low Molecular-Weight Water-Solubilizer)

To 1.8 mL of the chloroform solution of oleylamine-modified semiconductor nanoparticles (ZnAgInS), 1.8 mL of mercaptopropionic acid (MPA) was added as a low molecular-weight water-solubilizer, and the resulting mixture was stirred for 12 hours. Thereafter, 3.6 mL of 1 M Tris-HCl buffer (pH 8.0) was added thereto, and the semiconductor nanoparticles were extracted into an aqueous layer, after which the aqueous layer was recovered. Acetone in an amount of 7.2 mL was added thereto to precipitate the semiconductor nanoparticles, and the supernatant was removed by centrifugation at 4000 rpm for 5 minutes. Further, the semiconductor nanoparticles was redispersed using 2 mL of 1 M Tris-HCl buffer (pH 8.0), and 4 mL of acetone was added for precipitation, after which the supernatant was removed by centrifugation at 4000 rpm for 5 minutes. After repeating this operation once again, 1.8 mL of Milli-Q water was added to the resultant to redisperse the semiconductor nanoparticles, whereby an aqueous solution of semiconductor nanoparticles water-solubilized with MPA was obtained.

(Preparation of Water-Soluble Semiconductor Nanoparticle Complex Using Water-Soluble Polymer, 1)

Into 400 µL of the aqueous solution of semiconductor nanoparticles water-solubilized with MPA (MPA-NP), 0.5 mL of a 20 mg/mL aqueous solution of the water-soluble polymer (Polymers 1 to 15) was injected and stirred. At the same time, while adjusting the pH of the mixed solution to 10 by adding 1 N sodium hydroxide dropwise, the nanoparticles were complexated. Thereafter, purification by water dialysis (molecular weight cut-off: 25,000), ultrafiltration (Amicon Ultra-4, centrifugal filter devices, NMWL=100,000), and 0.2 µm filtering was performed (Complexes 1 to 3, 4-1, 10 to 17).

(Water-Solubilization of Semiconductor Nanoparticles and Complex Preparation Using Water-Soluble Polymer, 2)

Into 1.0 mL of the chloroform solution of oleylamine-modified semiconductor nanoparticles (ZnAgInS), a chloroform solution (1.0 mL) of a water-soluble polymer (10 mg/mL: Polymer 8-1, Polymer 9, 5 mg/mL: Polymer 8-2) was injected, and the resulting mixture was stirred for 24 hours in the presence of a DTT reducing agent. Thereafter, methanol dialysis and water dialysis (molecular weight cut-off: 25,000) were sequentially performed to thereby achieve water-solubilization as well as complex formation. Then, purification by ultrafiltration (Amicon Ultra-4, centrifugal filter devices, NMWL=100,000) and 0.2 µm filtering was performed (Complexes 8-1, 8-2, 9).

(Preparation of Water-Soluble Gold Nanoparticle Complex Using Water-Soluble Polymer)

Into 400 µL of an aqueous solution of citrate-reduced gold nanoparticles (available from Sigma, number average particle size: 5 nm), 0.5 mL of a 20 mg/mL aqueous solution of the polymer (Polymer 4) was injected and stirred. At the same time, while adjusting the pH of the mixed solution to 10 by adding 1 N sodium hydroxide dropwise, the nanoparticles were complexated. Thereafter, purification by water dialysis (molecular weight cut-off: 25,000), ultrafiltration (Amicon Ultra-4, centrifugal filter devices, NMWL=100,000), and 0.2 µm filtering was performed (Complex 4-2).

Example 7

Evaluation of Water-Soluble Nanoparticle Complex (Confirmation of Complexation and Analysis of Complex)

The complexation of the water-soluble nanoparticle complexes obtained in Example 6 was confirmed, in the cases of Complexes 1 to 7, in such a manner that, with the other mixing conditions fixed, a 20 mg/mL aqueous polymer solution (0.5 mL) was added to an aqueous solution (400 µL) of semiconductor nanoparticles (MPA-NP) or gold nanoparticles water-solubilized to the same concentration; the resulting mixture was stirred overnight; and then light scattering intensity, average particle size, and particle size distribution were measured by the dynamic light scattering (DLS) method. In the cases of Complexes 8 to 9, the complexation was confirmed in such a manner that, with the other mixing conditions fixed, a chloroform solution (1.0 mL) of a water-soluble polymer (10 mg/mL: Polymer 8-1, Polymer 9, 5 mg/mL: Polymer 8-2) was injected into a chloroform solution of oleylamine-modified semiconductor nanoparticles (ZnAgInS) (1.0 mL) of the same concentration; the resulting mixture was stirred overnight; methanol dialysis and water dialysis were sequentially performed; and then light scattering intensity distribution, diffusion coefficient, average particle size, and particle size distribution were measured by the dynamic light scattering (DLS) method.

For the measurement of various parameters for confirming the complexation, light scattering intensity distribution and diffusion coefficient were measured using Zeta potential/Particle size measurement system "ELS-Z1/Z2" manufactured by OTSUKA ELECTRONICS CO., LTD., and average particle size and particle size distribution were calculated by analyzing by the CUMULANT method. The results are shown in Table 1.

particle complex was not obtained because information on the complex by the DLS method was not obtained.

Figure 11:
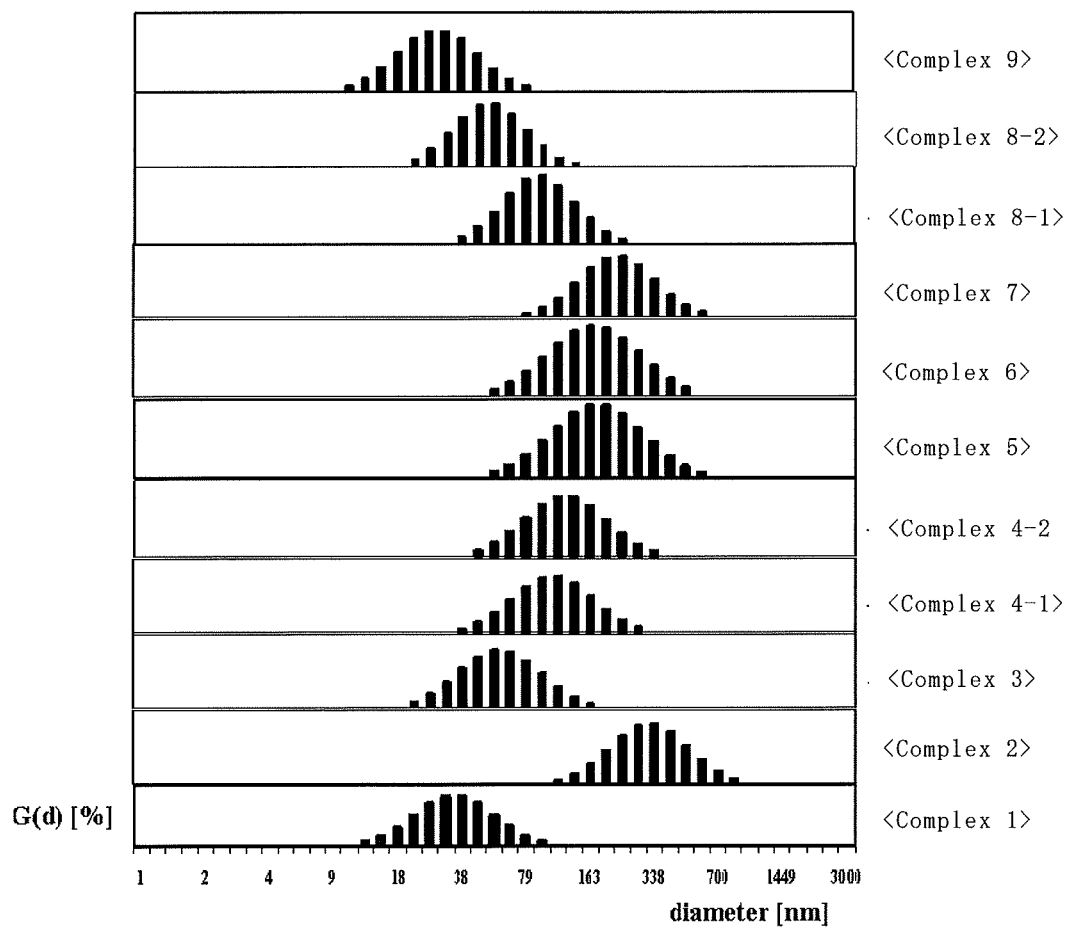
FIG. 11 is a graph representing the particle size distribution of a water-soluble nanoparticle complex analyzed from the measurements of dynamic light scattering (DLS) of the water-soluble nanoparticle complex in an aqueous solution.

When Polymer 1 was used, the average particle size of the water-soluble nanoparticle complex (d (nm)) was 36.9 nm and the particle size distribution was unimodal at 2.761e-001, confirming that a complex with a generally uniform particle size was formed (Complex 1 in FIG. 11).

When Polymer 2 was used, the average particle size of the water-soluble nanoparticle complex (d (nm)) was 261.2 nm and the particle size distribution was unimodal at 2.192e-001, confirming that a complex with a generally uniform particle size was formed (Complex 2 in FIG. 11).

When Polymer 3 was used, the average particle size of the water-soluble nanoparticle complex (d (nm)) was 46.2 nm and the particle size distribution was unimodal at 2.558e-001, confirming that a complex with a generally uniform particle size was formed (Complex 3 in FIG. 11).

When Polymer 4 was used, the average particle size of the water-soluble nanoparticle complex (d (nm)) was 83.9 nm and the particle size distribution was unimodal at 2.621e-001,

TABLE 1

Relationship between Composition of Water-Soluble Polymer and Complex

| | Composition of Water-Soluble Polymer | | | Complex | | |
|---|---|---|---|---|---|---|
| Polymer | Composition Ratio of Backbone Component (x:y [a + b]:z) | Degree of Polymerization (DP = x + y + z) | Complexation | Average Particle Size d (nm) | Particle Size Distribution | Diffusion Coefficient (cm$^2$/sec) |
| 1 | 0.40:0.59 [0.34 + 0.25]:0.01 | 22 | o (Complex 1) | 36.9 | 2.761e−001 | 1.324e−007 |
| 2 | 0.40:0.58 [0.30 + 0.28]:0.02 | 302 | o (Complex 2) | 261.2 | 2.192e−001 | 1.899e−008 |
| 3 | 0.27:0.55 [0.27 + 0.28]:0.18 | 43 | o (Complex 3) | 46.2 | 2.558e−001 | 1.067e−007 |
| 4 | 0.50:0.32 [0.32 + 0]:0.18 | 43 | o (Complex 4-1) | 83.9 | 2.621e−001 | 5.882e−008 |
| | | | o (Complex 4-2) | 98.5 | 2.473e−001 | 5.008e−008 |
| 5 | 0.66:0.22 [0.22 + 0]:0.12 | 93 | o (Complex 5) | 133.9 | 3.253e−001 | 3.704e−008 |
| 6 | 0.44:0.44 [0.44 + 0]:0.12 | 93 | o (Complex 6) | 126.5 | 3.370e−001 | 3.888e−008 |
| 7 | 0.55:0.43 [0.43 + 0]:0.02 | 93 | o (Complex 7) | 180.9 | 2.109e−001 | 2.712e−008 |
| 8 | 0.04.0.63 [0.63 + 0]:0.33 | 24 | o (Complex 8-1) | 76.2 | 1.898e−001 | 6.474e−008 |
| | | | o (Complex 8-2) | 42.8 | 1.936e−001 | 1.149e−007 |
| 9 | 0.11:0.24 [0.24 + 0]:0.65 | 24 | o (Complex 9) | 23.2 | 2.460e−001 | 2.127e−007 |
| 10 | 0:0 [0 + 0]:1 | 93 | x (Complex 10) | — | — | — |
| 11 | 0.98:0 [0 + 0]:0.02 | 302 | x (Complex 11) | — | — | — |
| 12 | 0.82:0 [0 + 0]:0.18 | 43 | x (Complex 12) | — | — | — |
| 13 | 0.99:0 [0 + 0]:0.01 | 22 | x (Complex 13) | — | — | — |
| 14 | 0:0.98 [0 + 0.98]:0.02 | 93 | x (Complex 14) | — | — | — |
| 15 | 0:0.99 [0.99 + 0]:0.01 | 22 | x (Complex 15) | — | — | — |
| 16 | 0:0.99 [0 + 0.99]:0.01 | 22 | x (Complex 16) | — | — | — |
| 17 | 0:0.98 [0 + 0.98]:0.02 | 302 | x (Complex 17) | — | — | — | o: complexated,
x: not complexated,
—: unevaluable

From the above results, for the water-soluble nanoparticle complexes obtained from a water-soluble polymer that satisfies the composition ratio of each segment in the ranges of x/(x+y+z)=0.01 to 0.70, y/(x+y+z)=0.20 to 0.70, and z/(x+y+z)=0.01 to 0.70, formation of the water-soluble nanoparticle complex was confirmed because information on the average particle size, the particle size distribution, and the like was obtained from the analysis using the DLS method. On the other hand, in the case where the composition ratio of each segment of the water-soluble polymer was outside the above-mentioned range, it was judged that the water-soluble nano-confirming that a complex with a generally uniform particle size was formed (Complex 4-1 in FIG. 11). When gold nanoparticles were used, the average particle size of the complex (d (nm)) was 98.5 nm and the particle size distribution was unimodal at 2.473e-001, confirming that a complex with a generally uniform particle size was formed (Complex 4-2 in FIG. 11).

When Polymer 5 was used, the average particle size of the water-soluble nanoparticle complex (d (nm)) was 133.9 nm and the particle size distribution was unimodal at 3.253e-001, confirming that a complex with a generally uniform particle size was formed (Complex 5 in FIG. 11).

When Polymer 6 was used, the average particle size of the water-soluble nanoparticle complex (d (nm)) was 126.5 nm and the particle size distribution was unimodal at 3.370e-001, confirming that a complex with a generally uniform particle size was formed (Complex 6 in FIG. 11).

When Polymer 7 was used, the average particle size of the water-soluble nanoparticle complex (d (nm)) was 180.9 nm and the particle size distribution was unimodal at 2.109e-001, confirming that a complex with a generally uniform particle size was formed (Complex 7 in FIG. 11).

When Polymer 8 was used and the polymer concentration was 5 mg/mL with other preparation conditions fixed, the average particle size of the water-soluble nanoparticle complex (d (nm)) was 76.2 nm and the particle size distribution was unimodal at 1.898e-001, confirming that a complex with a generally uniform particle size was formed (Complex 8-1 in FIG. 11). When the polymer concentration was 10 mg/mL with other preparation conditions fixed, the average particle size of the complex (d (nm)) was 42.8 nm and the particle size distribution was unimodal at 1.936e-001, confirming that a complex with a generally uniform particle size was formed (Complex 8-2 in FIG. 11).

When Polymer 9 was used, the average particle size of the water-soluble nanoparticle complex (d (nm)) was 23.2 nm and the particle size distribution was unimodal at 2.460e-001, confirming that a complex with a generally uniform particle size was formed (Complex 9 in FIG. 11).

Example 8

Transmission Electron Microscope (TEM) Measurements of Semiconductor Nanoparticles and Water-Soluble Nanoparticle Complex (TEM Measurements of Semiconductor Nanoparticles)

TEM observation of the oleylamine-modified semiconductor nanoparticles (ZnAgInS) synthesized in Example 6 was performed as described below. A chloroform solution of nanoparticles was added dropwise to a grid for TEM observation and left to stand until the chloroform was dried. The observation of the nanoparticles on the grid for TEM observation using a TEM (H-9000-UHR, manufactured by Hitachi Ltd.) at an accelerating voltage of 300 kV confirmed round-shaped fine particles. Its particle size was in the range of 2.1 to 2.7 nm, confirming that the oleylamine-modified semiconductor nanoparticles obtained had a particle size on the order of nanometers.

(TEM Measurements of Water-Soluble Nanoparticle Complex)

Figure 12:
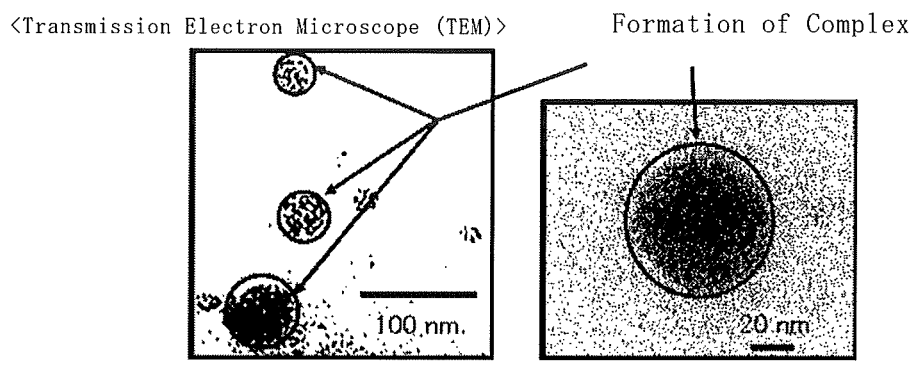
FIG. 12 is transmission electron micrographs (TEM) of a water-soluble nanoparticle complex in an aqueous solution.

To check the existence of the water-soluble nanoparticle complex (Complex 4-1) prepared in Example 6 and nanoparticles that were not accumulated and the form of the water-soluble nanoparticle complex, observation was carried out using a TEM (H-9000-UHR, manufactured by Hitachi Ltd.) by the dispersion method (the method in which a sample is diluted 20-fold and dried on a TEM mesh), confirming that a water-soluble nanoparticle complex in which a plurality of nanoparticles were accumulated was formed (FIG. 12).

Example 9

Fluorescence Measurements of Water-Soluble Nanoparticle Complex

Figure 13:
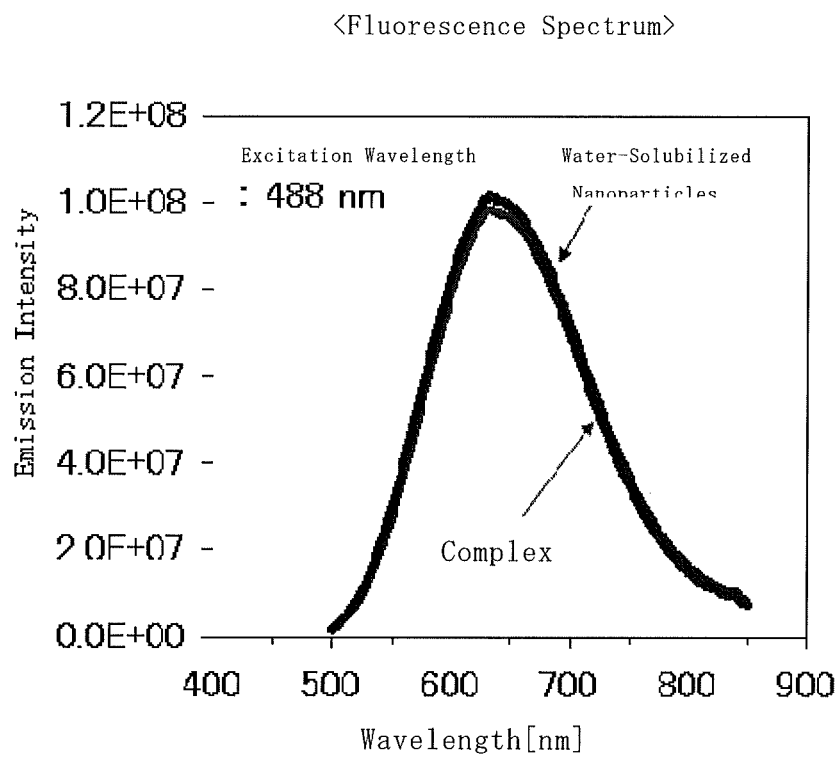
FIG. 13 is a graph representing the emission spectrum of a water-soluble nanoparticle complex in an aqueous solution.
Figure 14:
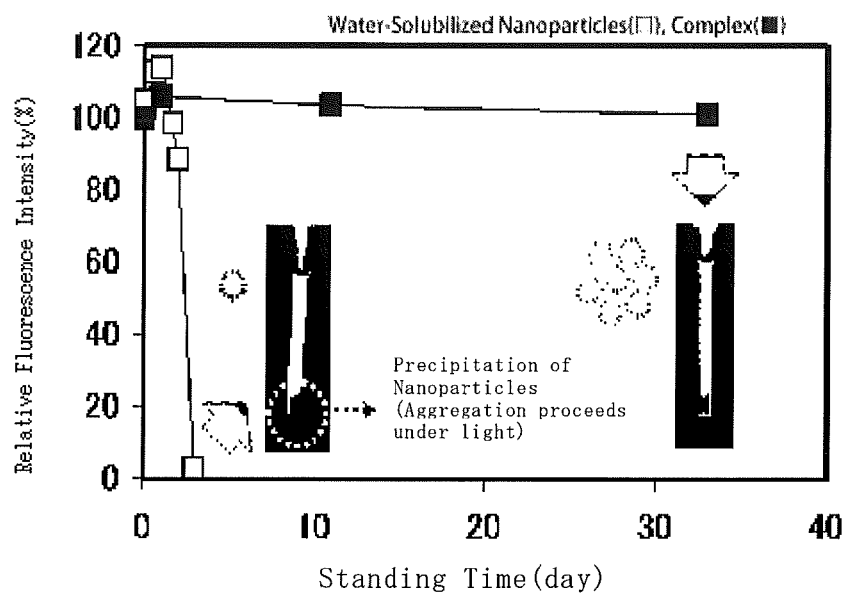
FIG. 14 is a graph representing the time stability of emission intensity of a water-soluble nanoparticle complex in an aqueous solution.

For the water-soluble nanoparticle complex (Complex 4-1) prepared in Example 6, the emission spectrum was measured. The measurements were made using a spectrofluorometer ("FluoroMax-3", manufactured by HORIBA JOBIN YVON). Under normal temperature, the measurements were made by irradiation with light at a wavelength of 488 nm (spectra collection wavelength: 500-850 nm), and the emission spectrum was observed, as shown in FIG. 13, with respect to each of the semiconductor nanoparticles water-solubilized with MPA (MPA-NP) and the water-soluble nanoparticle complex. It became clear from these results that the semiconductor nanoparticles were accumulated by the water-soluble polymer and complexated while maintaining their luminescence capability. Further, the comparison of the change in fluorescence intensity over time confirmed that the complex was superior to a single water-soluble nanoparticle also in water dispersion stability (FIG. 14).

Example 10

Figure 15:
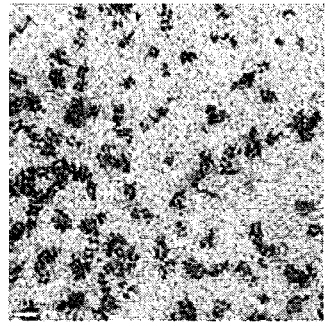
FIG. 15 is scanning transmission electron micrographs ((a) BF-STEM, (b) HAADF-STEM) of a water-soluble nanoparticle complex in an aqueous solution.
Figure 15:
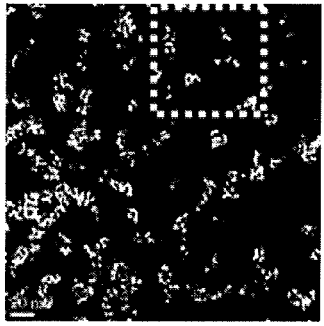
Figure 15:
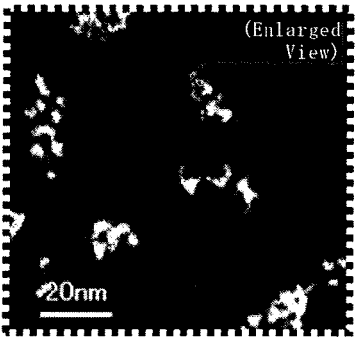

Scanning Transmission Electron Microscope (BF-STEM, HAADF-STEM) Measurements of Water-Soluble Nanoparticle Complex To check the existence of the water-soluble nanoparticle complex (Complex 9) prepared in Example 6 and nanoparticles that were not accumulated and the form of the water-soluble nanoparticle complex, observation was carried out using a field emission electron microscope (HRTEM) by the dispersion method (high-resolution grid: on a carbon support film made of Cu), confirming that a water-soluble nanoparticle complex in which a plurality of nanoparticles were accumulated was formed. Further, for the particles of about 2 to 3 nm exhibiting high contrast in an HAADF-STEM image, it was also confirmed by EDX analysis that Ag, In, Zn, and S, components of the nanoparticles, were contained (FIG. 15).

Example 11

Figure 16:
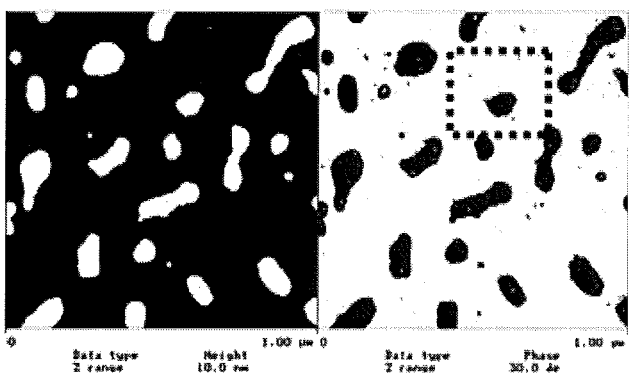
FIG. 16 is atomic force micrographs (AFM; (a) height image, (b) phase image) of a water-soluble nanoparticle complex in an aqueous solution.
Figure 16:
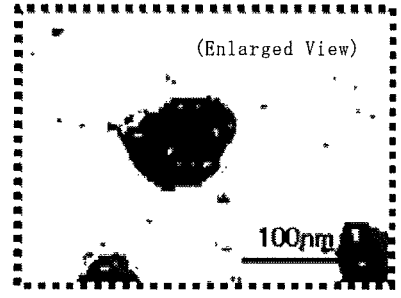

Atomic Force Microscope (AFM) Measurements of Water-Soluble Nanoparticle Complex To check the existence of the water-soluble nanoparticle complex (Complex 9) prepared in Example 6 and nanoparticles that were not accumulated and the form of the water-soluble nanoparticle complex, a dispersion was added dropwise onto mica, dried, and then observed by the phase imaging method, which is an application of atomic force microscope, to examine the state of the polymer containing semiconductor nanoparticles. In a height image, some bulging structures were observed on the mica. Many of them were structures having a height of about 10 nm which was considered to be an aggregation of polymers. In a phase image, bright contrasts with a size of about 10 nm were observed in a dark contrast at parts considered to be aggregated polymers; the way semiconductor nanoparticles were contained was considered to be captured. From the appearance of the phase image, it was confirmed that, in the field observed, almost all the polymers contained semiconductor nanoparticles (FIG. 16).

Example 12

Fluorescence Detection of Water-Soluble Nanoparticle Complex with DNA Chip

Figure 17:
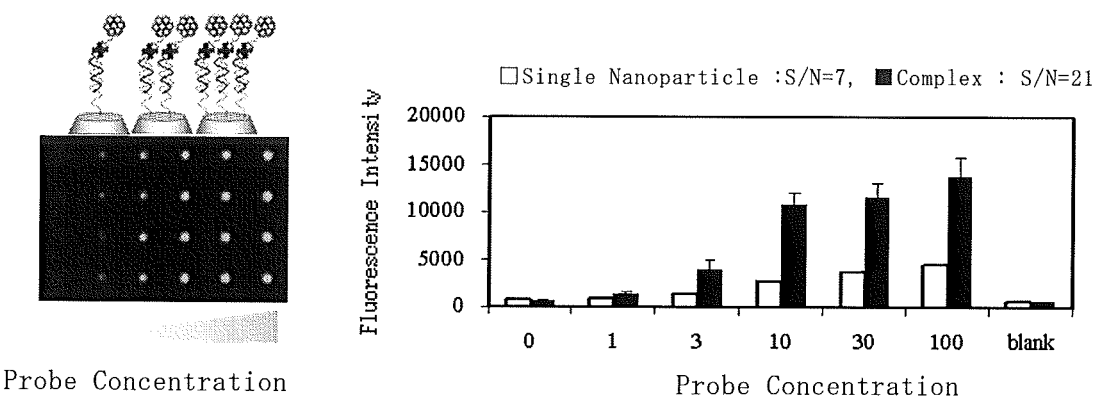
FIG. 17 is the result of fluorescence detection of a water-soluble nanoparticle complex on a DNA chip and a graph representing its fluorescence intensity.

For the water-soluble nanoparticle complex prepared in Example 6 (Complex 7), fluorescence detection on a DNA chip was performed using a DNA chip ("3D-Gene" (registered trademark) available from TORAY INDUSTRIES, INC.) as a model system for genetic detection (FIG. 17). After 10 pmol/chip of synthetic oligo-DNA to the 3' end of which biotin was added was hybridized at 37° C. with shaking overnight, washing was performed by the method recommended by "3D-Gene" (registered trademark). Next, NeutrAvidin or Cy5-labeled streptavidin (10 µg/mL, 1 M MES, 1 M NaCl, 0.05% Tween20) was allowed to stand and react at 37° C. For the washing method, the method recommended by "3D-Gene" (registered trademark) was used with respect to washing buffers and temperature, and washing time was each shortened to 2.5 minutes. Finally, in 1 M Tris-HCl containing 0.1% BSA, a single semiconductor nanoparticle having a biotinyl group on its surface and the complex were allowed to react. After the washing, excited fluorescence images of the single semiconductor nanoparticle and the water-soluble nanoparticle complex (ex 488 nm, em 614 nm) were acquired with a DNA chip scanner ("Scan Array Express", PerkinElmer Japan), and fluorescence intensities were quantified using GenePix Pro 6.0 (Molecular Device). For the fluorescence intensity at each probe concentration, the mean value of four spots was employed, and S/N ratios were calculated using 0 µM of a synthetic oligonucleotide as a background (BG). As a result, in the dyeing method using a sandwich structure of "(DNA) biotin-avidin-biotin (label)", the single semiconductor nanoparticles and the water-soluble nanoparticle complex were detected to have a fluorescence intensity that depends on the probe concentration, and it was confirmed that when labeled with the water-soluble nanoparticle complex, the S/N ratio exhibited was about three times or more higher than when labeled with the single semiconductor nanoparticles.

INDUSTRIAL APPLICABILITY

The water-soluble nanoparticle complex obtained using the water-soluble polymer is characterized in that a plurality of nanoparticles are accumulated in generally uniform particle size and that water dispersion stability and properties of the nanoparticles are maintained, and therefore it can be applied as a sensing reagent, for example, to biochemical applications such as biodiagnosis.

The invention claimed is:

1. A water-soluble polymer, comprising:
a repeating unit represented by Formula (1):

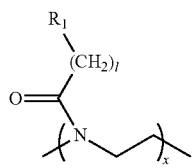

(wherein $R_1$ is —COOH, —OH, or —(OCH$_2$CH$_2$)$_p$R' (wherein R' is —COOH, —OH, —CH=CH$_2$, —C≡CH, or —N$_3$, and p is an integer from 1 to 30.), and l is an integer from 1 to 10.), a repeating unit represented by Formula (2):

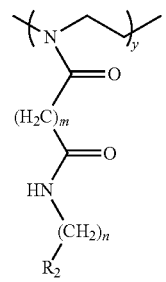

(wherein $R_2$ is —SR$_3$ or —NHR$_4$ (wherein R$_3$ is hydrogen or a thiol-protecting group selected from the group consisting of benzyl, methoxybenzyl, N-(acetyl)aminomethyl, t-butyl, methylbenzyl, 3,4-dimethylbenzyl, triphenylmethyl, benzhydryl, acetamidomethyl, carbomethoxysulfenyl, 3-nitro-2-pyridinesulfenyl, ethylcarbamoyl, 9-fluorenylmethyl, and pyridyl sulfide, and R$_4$ is hydrogen or an amino-protecting group selected from the group consisting of tert-butoxycarbonyl, benzyloxycarbonyl, 9-fluorenylmethyloxycarbonyl, 2,2,2-trichloroethoxycarbonyl, allyloxycarbonyl, phthaloyl, p-toluenesulfonyl, and 2-nitrobenzenesulfonyl); a, the number of repeating units containing —SR$_3$, and b, the number of repeating units containing —NHR$_4$, in y, the number of repeating units, satisfy b/a+b=0 to 0.60; and m and n are an integer from 1 to 10.), and
a repeating unit represented by Formula (3):

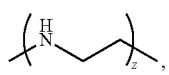

wherein x, the number of repeating units of Formula (1), y, the number of repeating units of Formula (2), and z, the number of repeating units of said Formula (3), satisfy x/(x+y+z)=0.01 to 0.70, y/(x+y+z)=0.20 to 0.70, and z/(x+y+z)=0.01 to 0.70.

2. The water-soluble polymer according to claim 1, wherein x, y, and z satisfy x+y+z=10 to 350.

3. The water-soluble polymer according to claim 2, wherein at least one end of a polymer main chain composed of the repeating units of Formulas (1), (2), and (3) comprises at least one functional group selected from the group consisting of —NH$_2$, —COOH, —OH, —SH, —CHO, and biotinyl.

4. A water-soluble nanoparticle complex, comprising the water-soluble polymer according to claim 2 and nanoparticles.

5. The water-soluble polymer according to claim 1, wherein at least one end of a polymer main chain composed of the repeating units of Formulas (1), (2), and (3) comprises at least one functional group selected from the group consisting of —NH$_2$, —COOH, —OH, —SH, —CHO, and biotinyl.

6. The water-soluble polymer according to claim 5, comprising —(OCH$_2$CH$_2$)$_p$— (wherein p is an integer from 1 to 120) as a spacer between said polymer main chain and said functional group.

7. A water-soluble nanoparticle complex, comprising the water-soluble polymer according to claim 4 and nanoparticles.

8. A water-soluble nanoparticle complex, comprising the water-soluble polymer according to claim 5 and nanoparticles.

9. A water-soluble nanoparticle complex, comprising the water-soluble polymer according to claim 1 and nanoparticles.

10. The water-soluble nanoparticle complex according to claim 9, wherein said water-soluble nanoparticle complex has an average particle size of 10 to 300 nm.

11. The water-soluble nanoparticle complex according to claim 10, wherein said nanoparticles have luminescence properties, plasmon absorption properties, or magnetic properties.

12. The water-soluble nanoparticle complex according to claim 10, wherein said nanoparticles are semiconductor nanoparticles.

13. The water-soluble nanoparticle complex according to claim 9, wherein said nanoparticles have luminescence properties, plasmon absorption properties, or magnetic properties.

14. A reagent containing the water-soluble nanoparticle complex according to claim 10.

15. The water-soluble nanoparticle complex according to claim 13, wherein said nanoparticles are semiconductor nanoparticles.

16. A reagent containing the water-soluble nanoparticle complex according to claim 13.

17. The water-soluble nanoparticle complex according to claim 9, wherein said nanoparticles are semiconductor nanoparticles.

18. The water-soluble nanoparticle complex according to claim 7, wherein said semiconductor nanoparticles are semiconductor nanoparticles comprising at least a Group 12 element of the periodic table and a Group 16 element of the periodic table, semiconductor nanoparticles comprising a Group 11 element of the periodic table, a Group 13 element of the periodic table, and a Group 16 element of the periodic table, or semiconductor nanoparticles comprising a Group 13 element of the periodic table and a Group 15 element of the periodic table.

19. A reagent containing the water-soluble nanoparticle complex according to claim 9.

20. A method of producing a water-soluble nanoparticle complex, comprising mixing nanoparticles and the water-soluble polymer according to claim 1 in an organic solvent.

* * * * *